United States Patent [19]
Conklin

[11] Patent Number: 6,143,720
[45] Date of Patent: Nov. 7, 2000

[54] LIPOCALIN HOMOLOGS

[75] Inventor: Darrell C. Conklin, Seattle, Wash.

[73] Assignee: ZymoGenetics, Inc., Seattle, Wash.

[21] Appl. No.: 09/432,335

[22] Filed: Nov. 2, 1999

Related U.S. Application Data

[62] Division of application No. 09/130,663, Aug. 6, 1998, Pat. No. 6,020,163.
[60] Provisional application No. 60/054,867, Aug. 6, 1997.
[51] Int. Cl.[7] .............................. A61K 38/00; C07K 1/00; C07H 21/04; C12P 21/06
[52] U.S. Cl. ........................ 514/12; 530/350; 530/402; 536/23.1; 536/23.4; 435/69.1
[58] Field of Search ...................... 530/350, 402; 536/23.1, 23.4; 514/12; 435/69.1

[56] References Cited

FOREIGN PATENT DOCUMENTS

WO 98/59049  12/1998  WIPO.

OTHER PUBLICATIONS

LIFESEQ™ Clone Information Results (INC1730294), Incyte Pharmaceuticals, Inc., 1996.
LIFESEQ™ Clone Information Results (INC1213903), Incyte Pharmaceuticals, Inc., 1996.
LIFESEQ™ Clone Information Results (INC1214269), Incyte Pharmaceuticals, Inc., 1996.
LIFESEQ™ Clone Information Results (INC1731309), Incyte Pharmaceuticals, Inc., 1996.
LIFESEQ™ Clone Information Results (INC3673491), Incyte Pharmaceuticals, Inc., 1997.
Hillier et al., WashU–Merck EST Project, Genbank Acc. No. AA460323, 1997.
Hillier et al., WashU–Merck EST Project, Genbank Acc. No. AA460385, 1997.
Strausberg, Cancer Genome Anatomy, Project, Genbank Acc. No. AA936288, 1997.
Strausberg, Cancer Genome Anatomy, Project, Genbank Acc. No. AA977608, 1997.

*Primary Examiner*—Karen Cochrane Carlson
*Assistant Examiner*—Devesh Srivastava
*Attorney, Agent, or Firm*—Deborah A. Sawislak

[57] ABSTRACT

The present invention is directed to polynucleotides and polypeptides for a novel member of the lipocalin family. The expression of this novel polynucleotide is restricted to testis and mammary gland, particularly breast tumor tissue. The polypeptide has been designated zlipo1. The present invention also includes antibodies to the zlipo1 polypeptides.

5 Claims, 5 Drawing Sheets

```
                                              3-10       A
                       |-- signal sequence  ---------------
         VEGP_HUMAN    MKPLLLAVSLGLIAALQA----HHLLASDEEIQDVSGTWYLKAMTVDREF 46
         EST          ---------------------------------------------------
         zlipo1        MKTLFLGVTLGLAAALS-------FTLEE--EDITGTWYVKAMVVDKDF 40
                                                b   b    b
         ERBP_RAT      MENIMPFALLGLCVGLAAGTEG--AVVKDFDISKFLGFWYEIAFASKMGT 48
                        *    :*.: :** *.    ..:    ... * ** *:. .

B          C          D
                                 ------    --------   ------------  --
         VEGP_HUMAN    PEMNLES-VTPMTLTTLEGGNLEAKVTMLISGRCQEVKAVLEKTDEPGKY 95
         EST          ----------------------
         zlipo1        PEDRRPRKVSPVKVTALGGGKLEATFTFMREDRCIQKKILMRKTEEPGKY 90
                        b b     b b                                      b
         ERBP_RAT      PGLAHKEEKMGAMVVELKENLLALTTTYYSEDHCVLEKVTATEGDGPAKF 98
                        *        :. *  . * . *   ...:*  *    : : *.*:

E      F        G          H
                       ---   --------  --------  -----------    -
         VEGP_HUMAN    TAD--GGKHVAYIIRSHVKDHYIFYCEGELHGKPVRGVKLVGRDPKNNLE 143
         zlipo1        SAY--GGRKLMYLQELPRRDHYIFYCKDQHHGGLLHMGKLVGRNSDTNRE 138
                        b b  b b        b b b         b b
         ERBP_RAT      QVTRLSGKKEVVVEATDYLTYAIIDITSLVAGAVHRTMKLYSRSLDDNGE 148
                        .  .*::   :       :*:  . *   :  ** .* . * *

A1         I
                       ---------------  ----
         VEGP_HUMAN    ALEDFEKAAGARGLSTESILIPRQSETCSPGSD------- 176
         zlipo1        ALEEFKKLVQRKGLSEEDIFTPLQTGSCVPEH-------- 170
         ERBP_RAT      ALYNFRKITSDHGFSETDLYILKHDLTCVKVLQSAAESRP 188
                       ** :*.*  .  :*:*  .:    . :*
```

```
                                        3-10         A
             |-- signal sequence    ----------------
VEGP_HUMAN   MKPLLLAVSLGLIAALQA----HHLLASDEEIQDVSGTWYLKAMTVDREF 46
EST          --------------------------------------------------
zlipo1       MKTLFLGVTLGLAAALS--------FTLEE--EDITGTWYVKAMVVDKDF 40
                                            b   b   b
ERBP_RAT     MENIMPFALLGLCVGLAAGTEG--AVVKDFDISKFLGFWYEIAFASKMGT 48
               *  :*.: :** *.       .. :    ... * **  *:. .

B         C           D
                    ------   ---------   ------------   --
VEGP_HUMAN   PEMNLES-VTPMTLTTLEGGNLEAKVTMLISGRCQEVKAVLEKTDEPGKY 95
EST          --------------------------
zlipo1       PEDRRPRKVSPVKVTALGGGKLEATFTFMREDRCIQKKILMRKTEEPGKY 90
                      b b      b b                          b
ERBP_RAT     PGLAHKEEKMGAMVVELKENLLALTTTYYSEDHCVLEKVTATEGDGPAKF 98
             *             :  *   *  .*    ..:*   *    : : *.*:

E        F         G              H
                ---   --------   -------     ----------     -
VEGP_HUMAN   TAD--GGKHVAYIIRSHVKDHYIFYCEGELHGKPVRGVKLVGRDPKNNLE 143
zlipo1       SAY--GGRKLMYLQELPRRDHYIFYCKDQHHGGLLHMGKLVGRNSDTNRE 138
                b b   b b         b b b          b b
ERBP_RAT     QVTRLSGKKEVVVEATDYLTYAIIDITSLVAGAVHRTMKLYSRSLDDNGE 148
                .*::    :       :*:   .  *    :  ** .*. . * *

A1             I
                ----------------   ----
VEGP_HUMAN   ALEDFEKAAGARGLSTESILIPRQSETCSPGSD------- 176
zlipo1       ALEEFKKLVQRKGLSEEDIFTPLQTGSCVPEH-------- 170
ERBP_RAT     ALYNFRKITSDHGFSETDLYILKHDLTCVKVLQSAAESRP 188
             ** :*.*  .  :*:*  .:      :   :*
```

LIPOCALIN HOMOLOGS

REFERENCE TO RELATED APPLICATIONS

This is a divisional application of application Ser. No. 09/130,663, filed Aug. 6, 1998, U.S. Pat. No. 6,020,163 which is related to Provisional Application No. 60/054,867, filed Aug. 6, 1997. Under 35 U.S.C. §199(e)(1), this application claims benefit of said provisional application.

BACKGROUND OF THE INVENTION

Lipocalins are small secreted proteins that are believed to be involved in the transport of small, hydrophobic molecules. The lipocalin family is characterized by the structural motif of a barrel formed by eight, anti-parallel, beta-sheets, which are arranged as two orthogonal sheets. The lipocalin family is diverse at the sequence level.

The most related members of the family share three characteristic conserved sequence motifs. Members of this group include: retinol-binding protein; purpurin; retinoic acid-binding protein; $\alpha_{2u}$-globin; major urinary protein; bilin-binding protein; α-crustacyanin; pregnancy protein 14; β-lactoglobulin; neutrophil lipocalin and choroid plexus protein. Outlier lipocalins are classified as such because they have 2 or less sequence motifs conserved and these proteins include: odorant-binding protein, von Ebner's gland protein, probasin and aphrodisin.

The lipocalins are members of the superfamily known as calycins, all of which are ligand-binding proteins for hydrophobic molecules. Other members of the calycin family are fatty acid-binding proteins (FABPs) and avidins. The members of this super-family share some conformational homology, with little sequence homology (Flower, *FEBS Letters* 354:7–11, 1994; and Flower, *J. Molec. Recognition* 8:185–195, 1995).

Von Ebner's gland protein, is also known as tear lipocalin, tear prealbumin or VEGP. It has been shown to be present in the acini of the prostate (Holzfeind et al., *FEBS Letters* 395:95–98, 1996), acinar cells of the lacrimal glands and von Ebner's gland (Holzfeind et al., *Exp. Eye Res.* 61:495–500, 1995). VEGP may also be present in salvia, nasal secretions and sweat. VEGP co-localizes with lysomsomes in serous acinar cells and is also present on polyribosomes from the ER and the Golgi apparatus.

Similar to other lipocalins, VEGP is a carrier for retinol or other small hydrophobic compounds. VEGP binds retinol in vitro, and is believed to have an antimicrobial function in the eye, partly because it binds long chain fatty acids which inhibit activation of lysozyme (Glasgow, *Arch. Clin. Exp. Ophthalmol.* 233:513–522, 1995). The protein may also inactivate enveloped viruses, help surface spreading of the lipid film in the eye and/or protein the epithelium.

Another member of the lipocalin family includes epididymal-retinoic acid binding protein (ERBP), which has tertiary structural homology to retinol-binding protein from human serum (Newcomer et al. *J. Biol. Chem.* 265:12876–12879, 1990). ERBP is believed to play and important role in maturation of the sperm as it passes through the epididymis. ERBP has been shown to bind a broad spectrum of retinoids, including retinol (vitamin A) retinal, retinyl acetate, β-ionone, cis retinoids, β-carotene, cholesterol, terpenoids, β-lonylideneacetate, long-chain esters of retinol and retinoic acid (Flower, *Biochem. J.* 318:1–14, 1996) in vivo and/or in vitro. The retinoids have been demonstrated to play important roles in cell differentiation and proliferation, as well as vision, reproductive biology, and mucus secretion. For a review of retinoids and their role in disease and maintenance of homeostasis, see, Goodman, D., *N. Engl. J. Med.* 310:1023–1031, 1984.

These and other aspects of the invention will become evident upon reference to the following detailed description of the invention and attached drawings.

SUMMARY OF THE INVENTION

In one aspect of the present invention provides a polynucleotide encoding a lipocalin homolog polypeptide comprising a sequence of amino acids that is at least 80% identical to the amino acid sequence as shown in SEQ ID NO: 2 from residue 1 or 17 to residue 170.

In another embodiment, the present invention provides a polynucleotide encoding a lipocalin homolog polypeptide comprising a sequence of polynucleotides as shown in SEQ ID NO: 1 from nucleotide 7 or 58 to nucleotide 516.

In another embodiment, the present invention provides a polynucleotide comprising a sequence polynucleotides as shown in SEQ ID NO: 5 from polynucleotide 1 or 52 to polynucleotide 510.

In another aspect, the present invention provides an expression vector comprising the following operably linked elements: a transcription promoter; a DNA segment encoding a lipocalin homolog polypeptide comprising a sequence of amino acid residues that is at least 80% identical to the amino acid sequence as shown in SEQ ID NO: 2 from amino acid residue 1 or 17 to residue 170; and a transcription terminator.

In another embodiment, the expression vector comprises a DNA segment, wherein the DNA segment comprises a sequence of polynucleotides as shown in SEQ ID NO: 1 from nucleotide 7 or 58 to nucleotide 516.

In another embodiment, expression vector comprises a DNA segment, wherein the DNA segment comprises a sequence of polynucleotides as shown in SEQ ID NO: 5 from nucleotide 1 or 52 to nucleotide 510.

In another aspect, the present invention provides cultured cell into which has been introduced an expression vector wherein said cell expresses the lipocalin homolog polypeptide encoded by the DNA segment of the expression vector.

In another aspect, the present invention provides a method of producing a polypeptide comprising: culturing a cell into which has been introduced an expression vector, whereby the cell expresses the lipocalin homolog polypeptide encoded by said DNA segment; and recovering said expressed polypeptide.

In another aspect, the present invention provides an isolated polypeptide comprising a sequence of amino acid residues that is at least 80% identical to the amino acid sequence as shown in SEQ ID NO: 2 from residue 1 or 17 to residue 170.

In another aspect, the present invention provides a pharmaceutical composition comprising a polypeptide comprising a sequence of amino acid residues that is at least 80% identical to the amino acid sequence as shown in SEQ ID NO: 2 from residue 1 or 17 to residue 170, in combination with a pharmaceutically acceptable vehicle.

In another aspect, the present invention provides an antibody that specifically binds to an epitope of a polypeptide comprising a sequence of amino acid residues that is at least 80% identical to the amino acid sequence as shown in SEQ ID NO: 2 from residue 17 to residue 170.

In another aspect, the present invention provides an oligonucleotide probe or primer comprising at least 14 contiguous nucleotides of a polynucleotide of SEQ ID NO: 1 or sequence complementary to SEQ ID NO: 1.

In another aspect, the present invention provides a method for detecting a genetic abnormality in a mammal comprising: obtaining a genetic sample from a mammal; incubating the genetic sample with a polynucleotide comprising at least 14 contiguous nucleotides of SEQ ID NO: 1 or the complement of SEQ ID NO: 1, under conditions wherein said polynucleotide will hybridize to the complementary polynucleotide sequence, produce a first reaction product; and comparing said first reaction product to a control reaction product, wherein a difference between said first reaction product and said control reaction product is indicative of a genetic abnormality in the patient.

BRIEF DESCRIPTION OF THE DRAWINGS

FIG. 1 is an illustration of a multiple alignment of human von Ebner's gland protein (VEGP hu; SEQ ID NO: 29), human zlipo1 (SEQ ID NO: 2, and rat epididymal-retinoic acid binding protein (ERBP rat; SEQ ID NO: 30). Within FIG. 1, "3–10" designates a short N-terminal helix; "A–I" are β-strands; "A1" designates a C-terminal α-helix; "b" designates ERBP ligand binding cavity; "*" designates conserved amino acids; ":" designates conserved amino acid substitutions; and "." designates less stringently conserved amino acid substitutions.

DETAILED DESCRIPTION OF THE INVENTION

Figure 2A:
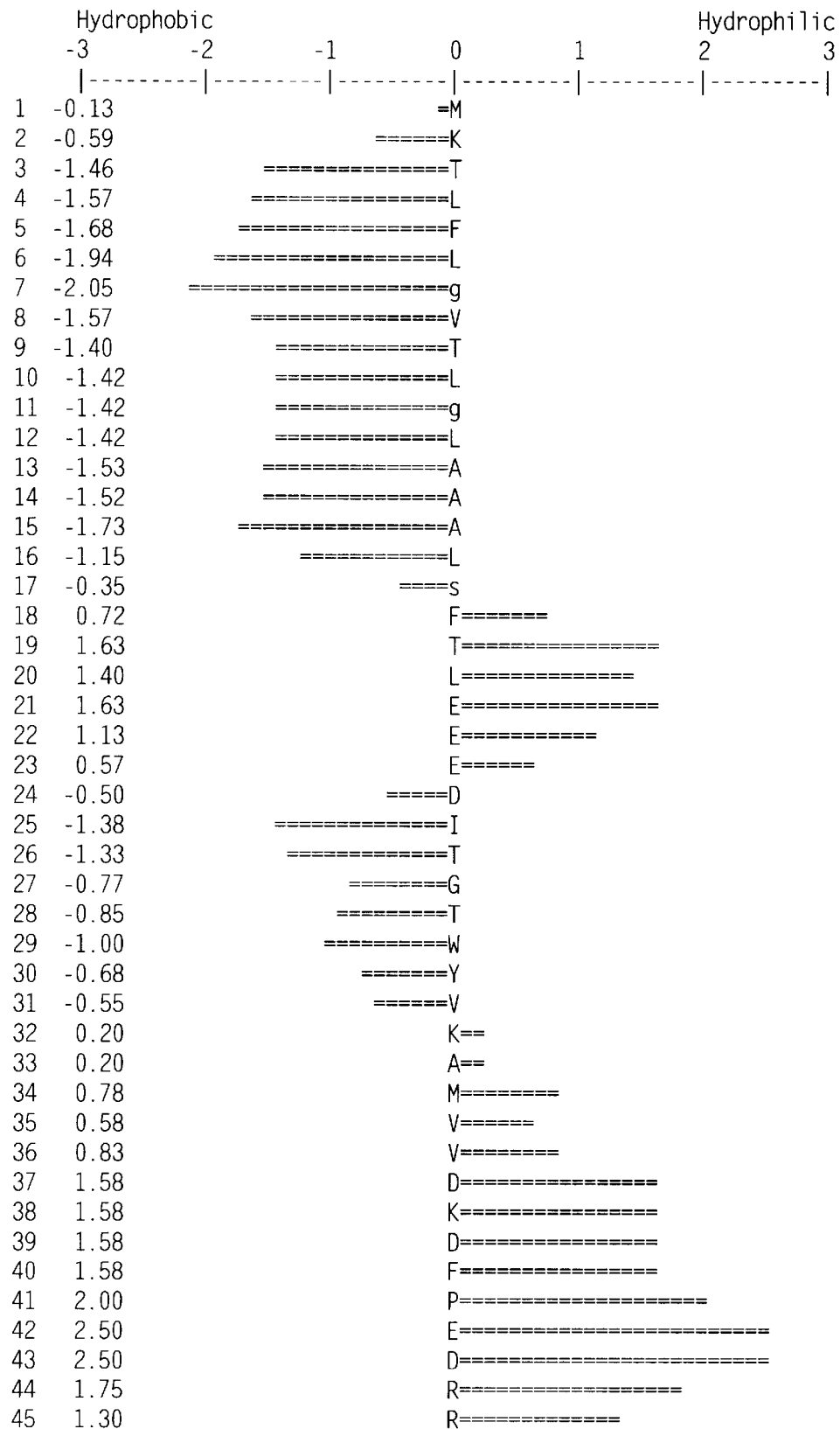
FIG. 2 is a Hopp/Woods hydrophilicity profile of the zlipo1 protein sequence shown in SEQ ID NO:2. The profile is based on a sliding six-residue window. Buried G, S, and T residues and exposed H, Y, and W residues were ignored. These residues are indicated in the figure by lower case letters.

Prior to setting forth the invention in detail, it may be helpful to the understanding thereof to define the following terms:

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a poly-histidine tract, protein A (Nilsson et al., *EMBO J.* 4:1075, 1985; Nilsson et al., *Methods Enzymol.* 198:3, 1991), glutathione S transferase (Smith and Johnson, *Gene* 67:31, 1988), Glu-Glu affinity tag (Grussenmeyer et al., *Proc. Natl. Acad. Sci. USA* 82:7952–4, 1985), substance P, Flag™ peptide (Hopp et al., *Biotechnology* 6:1204–10, 1988), streptavidin binding peptide, or other antigenic epitope or binding domain. See, in general, Ford et al., *Protein Expression and Purification* 2: 95–107, 1991. DNAs encoding affinity tags are available from commercial suppliers (e.g., Pharmacia Biotech, Piscataway, N.J.).

The term "allelic variant" is used herein to denote any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "complement/anti-complement pair" denotes non-identical moieties that form a non-covalently associated, stable pair under appropriate conditions. For instance, biotin and avidin (or streptavidin) are prototypical members of a complement/anti-complement pair. Other exemplary complement/anti-complement pairs include receptor/ligand pairs, antibody/antigen (or hapten or epitope) pairs, sense/antisense polynucleotide pairs, and the like. Where subsequent dissociation of the complement/anti-complement pair is desirable, the complement/anti-complement pair preferably has a binding affinity of $<10^9$ $M^{-1}$.

The term "complements of a polynucleotide molecule" is a polynucleotide molecule having a complementary base sequence and reverse orientation as compared to a reference sequence. For example, the sequence 5' ATGCACGGG 3' is complementary to 5' CCCGTGCAT 3'.

The term "contig" denotes a polynucleotide that has a contiguous stretch of identical or complementary sequence to another polynucleotide. Contiguous sequences are said to "overlap" a given stretch of polynucleotide sequence either in their entirety or along a partial stretch of the polynucleotide. For example, representative contigs to the polynucleotide sequence 5'-ATGGCTTAGCTT-3' are 5'-TAGCTTgagtct-3' and 3'-gtcgacTACCGA-5'.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

The term "expression vector" is used to denote a DNA molecule, linear or circular, that comprises a segment encoding a polypeptide of interest operably linked to additional segments that provide for its transcription. Such additional segments include promoter and terminator sequences, and may also include one or more origins of replication, one or more selectable markers, an enhancer, a polyadenylation signal, etc. Expression vectors are generally derived from plasmid or viral DNA, or may contain elements of both.

The term "isolated", when applied to a polynucleotide, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, *Nature* 316:774–78, 1985.

An "isolated" polypeptide or protein is a polypeptide or protein that is found in a condition other than its native environment, such as apart from blood and animal tissue. In a preferred form, the isolated polypeptide is substantially free of other polypeptides, particularly other polypeptides of animal origin. It is preferred to provide the polypeptides in a highly purified form, i.e., greater than 95% pure, more preferably greater than 99% pure. When used in this context, the term "isolated" does not exclude the presence of the same polypeptide in alternative physical forms, such as dimers or alternatively glycosylated or derivatized forms.

The term "operably linked", when referring to DNA segments, indicates that the segments are arranged so that they function in concert for their intended purposes, e.g., transcription initiates in the promoter and proceeds through the coding segment to the terminator.

The term "ortholog" denotes a polypeptide or protein obtained from one species that is the functional counterpart of a polypeptide or protein from a different species. Sequence differences among orthologs are the result of speciation.

"Paralogs" are distinct but structurally related proteins made by an organism. Paralogs are believed to arise through gene duplication. For example, α-globin, β-globin, and myoglobin are paralogs of each other.

A "polynucleotide" is a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. Sizes of polynucleotides are expressed as base pairs (abbreviated "bp"), nucleotides ("nt"), or kilobases ("kb"). Where the context allows, the latter two terms may describe polynucleotides that are single-stranded or double-stranded. When the term is applied to double-stranded molecules it is used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired. Such unpaired ends will in general not exceed 20 nt in length.

A "polypeptide" is a polymer of amino acid residues joined by peptide bonds, whether produced naturally or synthetically. Polypeptides of less than about 10 amino acid residues are commonly referred to as "peptides".

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

The term "receptor" denotes a cell-associated protein that binds to a bioactive molecule (i.e., a ligand) and mediates the effect of the ligand on the cell. Membrane-bound receptors are characterized by a multi-domain structure comprising an extracellular ligand-binding domain and an intracellular effector domain that is typically involved in signal transduction. Binding of ligand to receptor results in a conformational change in the receptor that causes an interaction between the effector domain and other molecule(s) in the cell. This interaction in turn leads to an alteration in the metabolism of the cell. Metabolic events that are linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids. In general, receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor).

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

The term "splice variant" is used herein to denote alternative forms of RNA transcribed from a gene. Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequence. The term splice variant is also used herein to denote a protein encoded by a splice variant of an mRNA transcribed from a gene.

Molecular weights and lengths of polymers determined by imprecise analytical methods (e.g., gel electrophoresis) will be understood to be approximate values. When such a value is expressed as "about" X or "approximately" X, the stated value of X will be understood to be accurate to ±10%.

All references cited herein are incorporated by reference in their entirety.

The proteins in this family have the structure of a single eight-stranded continuously hydrogen-bonded antiparallel barrel (Flower, *J. Molec. Recognition* 8:185–195, 1995). The β-strands (designated A–I in the Figure) form a calyx- or cup-shaped antiparallel β-barrel (Flower et al., *Protein Science* 2:753–761, 1993). The 3–10 helix, just N-terminal to the A strand, closes off one end of the barrel and with the A and B strands forming L1, is involved in formation of the of a cap for the internal ligand-binding site. Additional loops are formed by B–C (L2), C–D (L3), D–E (L4), E–F (L5), F–G (L6), G–H (L7), as shown in the Figure. Just C-terminal to the H strand (the end of the β-barrel) is an α-helix designated A1, which folds back against the barrel. Beyond the A1 structure is a strand (I), linked by β-sheet hydrogen bonding. These structural conformations are used to define the lipocalin family (Flower et al, ibid. 1993).

Analysis of the tissue distribution of the mRNA corresponding to this novel DNA showed that expression was specific to testis and mammary gland, particularly breast tumor tissue. The polypeptide has been designated zlipo1.

A single EST sequence was discovered and predicted to be a member of the lipocalin family. The EST was generated from a breast tumor cDNA library and contigs were later found in breast tumor cDNA libraries.

The nucleotide sequence of the N-terminal EST is described in SEQ ID NO. 1, polynucleotide number 7 to 192. The initiation Met is at position 1), and analysis of the DNA encoding a zlipo1 polypeptide (SEQ ID NO: 1) revealed an open reading frame encoding 170 amino acids (SEQ ID NO: 2) comprising a putative signal peptide of 17 amino acid residues (residue 1 to residue 17 of SEQ ID NO: 2) and a mature polypeptide of 153 amino acids (residue 18 to residue 170 of SEQ ID NO: 2), and is predicted to have a molecular weight of approximately 19 kD. Multiple alignment of zlipo1 with human von Ebner's gland protein (VEGP) revealed regions of high identity corresponding to amino acid residues 27–42, 57–67, 83–90, 104–111, 124–128, 139–145 and 150–55 of SEQ ID NO: 2, and as is shown in FIG. 1.

Lipocalins are characterized by a multi-domain structure comprising a ligand binding domain that is typically involved in binding small, hydrophobic molecules and a conserved cell-surface receptor-binding domain that is typically involved in binding some putative cell-surface receptor that may be common to more than one lipocalin and open end of the fold structure that forms a macromolecular complex, perhaps involving the cell-surface receptor. For example, retinol binding protein, a member of the lipocalin family, is characterized by the presence of a ligand binding site that binds retinol, a small hydrophobic molecule. As shown in the Figure, rat epididymal-retinoic acid binding protein (ERBP-rat) has homology to zlipo1 as well. Therefore, based on homology with other lipocalins, beta strand formation is predicted for regions designated as A–I in FIG. 1 and corresponds to amino acid residues 23–36, 54–59, 62–69, 74–83, 89–93, 97–103, 109–115, 123–132, and 158–161, as shown in SEQ ID NO: 2.

Based on the homology revealed between the rat ERBP and zlipo1, a putative ligand-binding cavity is formed that includes amino acid residues 22 (Glu), 25 (Ile), 29 (Trp), 53 (Lys), 55 (Thr), 62 (Leu), 64 (Ala), 90 (Tyr), 92 (Ala), 97 (Lys), 99 (Met), 110 (Tyr), 112 (Phe), 114 (Cys), 127 (Lys) and 129 (Val), as shown in SEQ ID NO: 2 and in FIG. 1 is represented as "b".

Additional characteristic features of zlipo1 include multiple dibasic amino acids (Arg and Lys) found at amino acid residues 44–45 (Arg Arg), 47–48 (Arg Lys), 82–83 (Arg Lys), 96–97 (Arg Lys) 106–107 (Arg Arg) 144–145 (Lys Lys) and 149–150 (Arg Lys). These dibasic cleavage sites are prevalent cleavage sites for prohormone convertase. However, because there are limited dibasic combinations (i.e., Lys Lys; Lys Arg; Arg Arg and Arg Lys) monobasic cleavage sites are observed as well in many polypeptides. Cleavage at dibasic prohormone convertase sites resulting in short peptides is common in generating short neuropeptides from larger polypeptides.

The highly conserved amino acids in the a significant domain, region or motif of zlipo1 can be used as a tool to identify new family members. For instance, reverse transcription-polymerase chain reaction (RT-PCR) can be used to amplify sequences encoding the conserved regions, e.g., beta-strand regions and ligand-binding cavity, from RNA obtained from a variety of tissue sources or cell lines. In particular, highly degenerate primers designed from the zlipo1 sequences are useful for this purpose.

The present invention also provides polynucleotide molecules, including DNA and RNA molecules, that encode the zlipo1 polypeptides disclosed herein. Those skilled in the art will readily recognize that, in view of the degeneracy of the genetic code, considerable sequence variation is possible among these polynucleotide molecules. SEQ ID NO:5 is a degenerate DNA sequence that encompasses all DNAs that encode the zlipo1 also provides all RNA sequences encoding SEQ ID NO:2 by substituting U for T. Thus, zlipo1 polypeptide-encoding polynucleotides comprising nucleotide 1 to nucleotide 510 of SEQ ID NO:5 and their RNA equivalents are contemplated by the present invention. Table 1 sets forth the one-letter codes used within SEQ ID NO:5 to denote degenerate nucleotide positions. "Resolutions" are the nucleotides denoted by a code letter. "Complement" indicates the code for the complementary nucleotide(s). For example, the code Y denotes either C or T, and its complement R denotes A or G, A being complementary to T, and G being complementary to C.

TABLE 1

| Nucleotide | Resolution | Complement | Resolution |
|---|---|---|---|
| A | A | T | T |
| C | C | G | G |
| G | G | C | C |
| T | T | A | A |
| R | A\|G | Y | C\|T |
| Y | C\|T | R | A\|G |
| M | A\|C | K | G\|T |
| K | G\|T | M | A\|C |
| S | C\|G | S | C\|G |
| W | A\|T | W | A\|T |
| H | A\|C\|T | D | A\|G\|T |
| B | C\|G\|T | V | A\|C\|G |
| V | A\|C\|G | B | C\|G\|T |
| D | A\|G\|T | H | A\|C\|T |
| N | A\|C\|G\|T | N | A\|C\|G\|T |

The degenerate codons used in SEQ ID NO:5, encompassing all possible codons for a given amino acid, are set forth in Table 2.

TABLE 2

| Amino Acid | One Letter Code | Codons | | | | | Degenerate Codon |
|---|---|---|---|---|---|---|---|
| Cys | C | TGC | TGT | | | | TGY |
| Ser | S | AGC | AGT | TCA | TCC | TCG TCT | WSN |
| Thr | T | ACA | ACC | ACG | ACT | | ACN |
| Pro | P | CCA | CCC | CCG | CCT | | CCN |
| Ala | A | GCA | GCC | GCG | GCT | | GCN |
| Gly | G | GGA | GGC | GGG | GGT | | GGN |
| Asn | N | AAC | AAT | | | | AAY |
| Asp | D | GAC | GAT | | | | GAY |
| Glu | E | GAA | GAG | | | | GAR |
| Gln | Q | CAA | CAG | | | | CAR |
| His | H | CAC | CAT | | | | CAY |
| Arg | R | AGA | AGG | CGA | CGC | CGG CGT | MGN |
| Lys | K | AAA | AAG | | | | AAR |
| Met | M | ATG | | | | | ATG |
| Ile | I | ATA | ATC | ATT | | | ATH |
| Leu | L | CTA | CTC | CTG | CTT | TTA TTG | YTN |
| Val | V | GTA | GTC | GTG | GTT | | GTN |
| Phe | F | TTC | TTT | | | | TTY |
| Tyr | Y | TAC | TAT | | | | TAY |
| Trp | W | TGG | | | | | TGG |
| Ter | . | TAA | TAG | TGA | | | TRR |
| Asn\|Asp | B | | | | | | RAY |
| Glu\|Gln | Z | | | | | | SAR |
| Any | X | | | | | | NNN |

One of ordinary skill in the art will appreciate that some ambiguity is introduced in determining a degenerate codon, representative of all possible codons encoding each amino acid. For example, the degenerate codon for serine (WSN) can, in some circumstances, encode arginine (AGR), and the degenerate codon for arginine (MGN) can, in some circumstances, encode serine (AGY). A similar relationship exists between codons encoding phenylalanine and leucine.

Thus, some polynucleotides encompassed by the degenerate sequence may encode variant amino acid sequences, but one of ordinary skill in the art can easily identify such variant sequences by reference to the amino acid sequence of SEQ ID NO:2. Variant sequences can be readily tested for functionality as described herein.

It is to be recognized that according to the present invention, when a polynucleotide is claimed as described herein, it is understood that what is claimed are both the sense strand, the anti-sense strand, and the DNA as double-stranded having both the sense and anti-sense strand annealed together by their respective hydrogen bonds. Also claimed is the messenger RNA (mRNA) which encodes the polypeptides of the president invention, and which mRNA is encoded by the cDNA described herein. Messenger RNA (mRNA) will encode a polypeptide using the same codons as those defined herein, with the exception that each thymine nucleotide (T) is replaced by a uracil nucleotide (U).

One of ordinary skill in the art will also appreciate that different species can exhibit "preferential codon usage." In general, see, Grantham, et al., *Nuc. Acids Res.* 8:1893–912, 1980; Haas, et al. *Curr. Biol.* 6:315–24, 1996; Wain-Hobson, et al., *Gene* 13:355–64, 1981; Grosjean and Fiers, *Gene* 18:199–209, 1982; Holm, *Nuc. Acids Res.* 14:3075–87, 1986; Ikemura, *J. Mol. Biol.* 158:573–97, 1982. As used herein, the term "preferential codon usage" or "preferential codons" is a term of art referring to protein translation codons that are most frequently used in cells of a certain species, thus favoring one or a few representatives of the possible codons encoding each amino acid (See Table 2). For example, the amino acid Threonine (Thr) may be encoded by ACA, ACC, ACG, or ACT, but in mammalian cells ACC is the most commonly used codon; in other species, for example, insect cells, yeast, viruses or bacteria, different Thr codons may be preferential. Preferential codons for a particular species can be introduced into the polynucleotides of the present invention by a variety of methods known in the art. Introduction of preferential codon sequences into recombinant DNA can, for example, enhance production of the protein by making protein translation more efficient within a particular cell type or species. Therefore, the degenerate codon sequence disclosed in SEQ ID NO:5 serves as a template for optimizing expression of polynucleotides in various cell types and species commonly used in the art and disclosed herein. Sequences containing preferential codons can be tested and optimized for expression in various species, and tested for functionality as disclosed herein.

Within preferred embodiments of the invention the isolated polynucleotides will hybridize to similar sized regions of SEQ ID NO:1, or a sequence complementary thereto, under stringent conditions. In general, stringent conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Typical stringent conditions are those in which the salt concentration is up to about 0.03 M at pH 7 and the temperature is at least about 60° C.

As previously noted, the isolated polynucleotides of the present invention include DNA and RNA. Methods for preparing DNA and RNA are well known in the art. In general, RNA is isolated from a tissue or cell that produces large amounts of zlipo1 RNA. Such tissues and cells are identified by Northern blotting (Thomas, *Proc. Natl. Acad. Sci. USA* 77:5201, 1980), and include testis, mammary gland, and breast tumor tissue. Total RNA can be prepared using guanidinium isothiocyanate extraction followed by isolation by centrifugation in a CsCl gradient (Chirgwin et al., *Biochemistry* 18:52–94, 1979). Poly (A)$^+$ RNA is prepared from total RNA using the method of Aviv and Leder (*Proc. Natl. Acad. Sci. USA* 69:1408–1412, 1972). Complementary DNA (cDNA) is prepared from poly(A)$^+$ RNA using known methods. In the alternative, genomic DNA can be isolated. Polynucleotides encoding zlipo1 polypeptides are then identified and isolated by, for example, hybridization or PCR.

A full-length clone encoding zlipo1 can be obtained by conventional cloning procedures. Complementary DNA (cDNA) clones are preferred, although for some applications (e.g., expression in transgenic animals) it may be preferable to use a genomic clone, or to modify a cDNA clone to include at least one genomic intron. Methods for preparing cDNA and genomic clones are well known and within the level of ordinary skill in the art, and include the use of the sequence disclosed herein, or parts thereof, for probing or priming a library. Expression libraries can be probed with antibodies to zlipo1, receptor fragments, or other specific binding partners.

The polynucleotides of the present invention can also be synthesized using methods that are well known to those ordinarily skilled the art. See Glick and Pasternak, *Molecular Biotechnology, Principles & Applications of Recombinant DNA,* (ASM Press, Washington, D.C. 1994); Itakura et al., *Annu. Rev. Biochem.* 53: 323–56, 1984 and Climie et al., *Proc. Natl. Acad. Sci. USA* 87:633–7, 1990.

The present invention further provides counterpart polypeptides and polynucleotides from other species (orthologs). These species include, but are not limited to mammalian, avian, amphibian, reptile, fish, insect and other vertebrate and invertebrate species. Of particular interest are zlipo1 orthologous polypeptides from other mammalian species, including murine, porcine, ovine, bovine, canine, feline, equine, and other primate polypeptides. Orthologs of human zlipo1 can be cloned using information and compositions provided by the present invention in combination with conventional cloning techniques. For example, a cDNA can be cloned using mRNA obtained from a tissue or cell type that expresses zlipo1 as disclosed herein. Suitable sources of mRNA can be identified by probing Northern blots with probes designed from the sequences disclosed herein. A library is then prepared from mRNA of a positive tissue or cell line. A zlipo1-encoding cDNA can then be isolated by a variety of methods, such as by probing with a complete or partial human cDNA or with one or more sets of degenerate probes based on the disclosed sequences. A cDNA can also be cloned using the polymerase chain reaction, or PCR (Mullis, U.S. Pat. No. 4,683,202), using primers designed from the representative human zlipo1 sequences disclosed herein. Within an additional method, the cDNA library can be used to transform or transfect host cells, and expression of the cDNA of interest can be detected with an antibody to zlipo1polypeptide. Similar techniques can also be applied to the isolation of genomic clones.

Those skilled in the art will recognize that the sequence disclosed in SEQ ID NO:1 represents a single allele of human zlipo1 and that allelic variation and alternative splicing are expected to occur. cDNAs generated from alternatively spliced mRNAs, which retain the properties of the zlipo1 polypeptide are included within the scope of the present invention, as are polypeptides encoded by such cDNAs and mRNAs. Allelic variants and splice variants of these sequences can be cloned by probing cDNA or genomic libraries from different individuals or tissues according to standard procedures known in the art.

The present invention also provides isolated zlipo1 polypeptides that are substantially homologous to the polypeptides of SEQ ID NO:2 and their orthologs. The term "substantially homologous" is used herein to denote polypeptides having at least 60%, preferably at least 80%, more preferably at least 90% or greater, sequence identity to the sequences shown in SEQ ID NO:2 or their orthologs. Such polypeptides will more preferably be at least 90% identical, and most preferably 95%, 96%, 97%, 98% or 99% identical to SEQ ID NO:2 or its orthologs. The present invention thus includes polypeptides of from 152 to 170 amino acid residues that comprise a sequence that is at least 60%, preferably at least 80%, and more preferably 90% or more identical to the corresponding region of SEQ ID NO:2. Percent sequence identity is determined by conventional methods. See, for example, Altschul et al., *Bull. Math. Bio.* 48: 603–616, 1986 and Henikoff and Henikoff, *Proc. Natl. Acad. Sci. USA* 89:10915–10919, 1992. Briefly, two amino acid sequences are aligned to optimize the alignment scores using a gap opening penalty of 10, a gap extension penalty of 1, and the "blosum 62" scoring matrix of Henikoff and Henikoff (ibid.) as shown in Table 3 (amino acids are indicated by the standard one-letter codes).

The percent identity is then calculated as:

$$\frac{\text{Total number of identical matches}}{\text{[length of the longer sequence plus the number of gaps introduced into the longer sequence in order to align the two sequences]}} \times 100$$

Sequence identity of polynucleotide molecules is determined by similar methods using a ratio as disclosed above.

Variant zlipo1 polypeptides or substantially homologous zlipo1 polypeptides are characterized as having one or more amino acid substitutions, deletions or additions. These changes are preferably of a minor nature, that is conservative amino acid substitutions (see Table 4) and other substitutions that do not significantly affect the folding or activity of the polypeptide; small deletions, typically of one to about 30 amino acids; and small amino- or carboxyl-terminal extensions, such as an amino-terminal methionine residue, a small linker peptide of up to about 20–25 residues, or an affinity tag. Polypeptides comprising affinity tags can further comprise a proteolytic cleavage site between the zlipo1 polypeptide and the affinity tag. Preferred such sites include thrombin cleavage sites and factor Xa cleavage sites.

TABLE 4

| Conservative amino acid substitutions | |
|---|---|
| Basic: | arginine |
| | lysine |
| | histidine |
| Acidic: | glutamic acid |
| | aspartic acid |
| Polar: | glutamine |
| | asparagine |
| Hydrophobic: | leucine |
| | isoleucine |
| | valine |
| Aromatic: | phenylalanine |
| | tryptophan |
| | tyrosine |
| Small: | glycine |
| | alanine |

TABLE 3

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | -1 | 5 | | | | | | | | | | | | | | | | | | |
| N | -2 | 0 | 6 | | | | | | | | | | | | | | | | | |
| D | -2 | -2 | 1 | 6 | | | | | | | | | | | | | | | | |
| C | 0 | -3 | -3 | -3 | 9 | | | | | | | | | | | | | | | |
| Q | -1 | 1 | 0 | 0 | -3 | 5 | | | | | | | | | | | | | | |
| E | -1 | 0 | 0 | 2 | -4 | 2 | 5 | | | | | | | | | | | | | |
| G | 0 | -2 | 0 | -1 | -3 | -2 | -2 | 6 | | | | | | | | | | | | |
| H | -2 | 0 | 1 | -1 | -3 | 0 | 0 | -2 | 8 | | | | | | | | | | | |
| I | -1 | -3 | -3 | -3 | -1 | -3 | -3 | -4 | -3 | 4 | | | | | | | | | | |
| L | -1 | -2 | -3 | -4 | -1 | -2 | -3 | -4 | -3 | 2 | 4 | | | | | | | | | |
| K | -1 | 2 | 0 | -1 | -3 | 1 | 1 | -2 | -1 | -3 | -2 | 5 | | | | | | | | |
| M | -1 | -1 | -2 | -3 | -1 | 0 | -2 | -3 | -2 | 1 | 2 | -1 | 5 | | | | | | | |
| F | -2 | -3 | -3 | -3 | -2 | -3 | -3 | -3 | -1 | 0 | 0 | -3 | 0 | 6 | | | | | | |
| P | -1 | -2 | -2 | -1 | -3 | -1 | -1 | -2 | -2 | -3 | -3 | -1 | -2 | -4 | 7 | | | | | |
| S | 1 | -1 | 1 | 0 | -1 | 0 | 0 | 0 | -1 | -2 | -2 | 0 | -1 | -2 | -1 | 4 | | | | |
| T | 0 | -1 | 0 | -1 | -1 | -1 | -1 | -2 | -2 | -1 | -1 | -1 | -1 | -2 | -1 | 1 | 5 | | | |
| W | -3 | -3 | -4 | -4 | -2 | -2 | -3 | -2 | -2 | -3 | -2 | -3 | -1 | 1 | -4 | -3 | -2 | 11 | | |
| Y | -2 | -2 | -2 | -3 | -2 | -1 | -2 | -3 | 2 | -1 | -1 | -2 | -1 | 3 | -3 | -2 | -2 | 2 | 7 | |
| V | 0 | -3 | -3 | -3 | -1 | -2 | -2 | -3 | -3 | 3 | 1 | -2 | 1 | -1 | -2 | -2 | 0 | -3 | -1 | 4 |

TABLE 4-continued

Conservative amino acid substitutions serine
threonine
methionine

The present invention further provides a variety of other polypeptide fusions and related multimeric proteins comprising one or more polypeptide fusions. For example, a zlipo1 polypeptide can be prepared as a fusion to a dimerizing protein as disclosed in U.S. Pat. Nos. 5,155,027 and 5,567,584. Preferred dimerizing proteins in this regard include immunoglobulin constant region domains. Immunoglobulin- zlipo1 polypeptide fusions can be expressed in genetically engineered cells to produce a variety of multimeric zlipo1 analogs. Auxiliary domains can be fused to zlipo1 polypeptides to target them to specific cells, tissues, or macromolecules (e.g., collagen). For example, a zlipo1 polypeptide or protein could be targeted to a predetermined cell type by fusing a zlipo1 polypeptide to a ligand that specifically binds to a receptor on the surface of the target cell. In this way, polypeptides and proteins can be targeted for therapeutic or diagnostic purposes. A zlipo1 polypeptide can be fused to two or more moieties, such as an affinity tag for purification and a targeting domain. Polypeptide fusions can also comprise one or more cleavage sites, particularly between domains. See, Tuan et al., *Connective Tissue Research* 34:1–9, 1996.

The proteins of the present invention can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methylglycine, allo-threonine, methylthreonine, hydroxyethylcysteine, hydroxyethylhomocysteine, nitroglutamine, homoglutamine, pipecolic acid, thiazolidine carboxylic acid, dehydroproline, 3- and 4-methylproline, 3,3-dimethylproline, tert-leucine, norvaline, 2-azaphenylalanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell-free system comprising an *E. coli* S30 extract and commercially available enzymes and other reagents. Proteins are purified by chromatography. See, for example, Robertson et al., *J. Am. Chem. Soc.* 113:2722, 1991; Ellman et al., *Methods Enzymol.* 202:301, 1991; Chung et al., *Science* 259:806–809, 1993; and Chung et al., *Proc. Natl. Acad. Sci. USA* 90:10145–10149, 1993). In a second method, translation is carried out in Xenopus oocytes by microinjection of mutated mRNA and chemically aminoacylated suppressor tRNAs (Turcatti et al., *J. Biol. Chem.* 271:19991–19998, 1996). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. See, Koide et al., *Biochem.* 33:7470–7476, 1994. Naturally occurring amino acid residues can be converted to non-naturally occurring species by in vitro chemical modification. Chemical modification can be combined with site-directed mutagenesis to further expand the range of substitutions (Wynn and Richards, *Protein Sci.* 2:395–403, 1993).

A limited number of non-conservative amino acids, amino acids that are not encoded by the genetic code, non-naturally occurring amino acids, and unnatural amino acids may be substituted for zlipo1 amino acid residues.

Essential amino acids in the polypeptides of the present invention can be identified according to procedures known in the art, such as site-directed mutagenesis or alanine-scanning mutagenesis (Cunningham and Wells, *Science* 244: 1081–1085, 1989; Bass et al., *Proc. Natl. Acad. Sci. USA* 88:4498–502, 1991). In the latter technique, single alanine mutations are introduced at every residue in the molecule, and the resultant mutant molecules are tested for biological activity as disclosed below to identify amino acid residues that are critical to the activity of the molecule. See also, Hilton et al., *J. Biol. Chem.* 271:4699–4708, 1996. For example, sites of ligand-receptor interaction can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., *Science* 255:306–312, 1992; Smith et al., *J. Mol. Biol.* 224:899–904, 1992; Wlodaver et al., *FEBS Lett.* 309:59–64, 1992. The identities of essential amino acids can also be inferred from analysis of homologies with related lipocalins.

Amino acid sequence changes are made in zlipo1 polypeptides so as to minimize disruption of higher order structure essential to biological activity. In this regard, it is generally preferred to retain the overall hydrophilicity profile of the natural sequence. A hydrophilicity profile of the sequence shown in SEQ ID NO:2 is shown in FIG. 1.

Multiple amino acid substitutions can be made and tested using known methods of mutagenesis and screening, such as those disclosed by Reidhaar-Olson and Sauer (*Science* 241:53–57, 1988) or Bowie and Sauer (*Proc. Natl. Acad. Sci. USA* 86:2152–2156, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., *Biochem.* 30:10832–10837, 1991; Ladner et al., U.S. Pat. No. 5,223,409; Huse, WIPO Publication WO 92/06204) and region-directed mutagenesis (Derbyshire et al., *Gene* 46:145, 1986; Ner et al., *DNA* 7:127, 1988).

Variants of the disclosed zlipo1 DNA and polypeptide sequences can be generated through DNA shuffling as disclosed by Stemmer, *Nature* 370:389–91, 1994, Stemmer, *Proc. Natl. Acad. Sci. USA* 91:10747–51, 1994 and WIPO Publication WO 97/20078. Briefly, variant DNAs are generated by in vitro homologous recombination by random fragmentation of a parent DNA followed by reassembly using PCR, resulting in randomly introduced point mutations. This technique can be modified by using a family of parent DNAs, such as allelic variants or DNAs from different species, to introduce additional variability into the process. Selection or screening for the desired activity, followed by additional iterations of mutagenesis and assay provides for rapid "evolution" of sequences by selecting for desirable mutations while simultaneously selecting against detrimental changes.

Mutagenesis methods as disclosed herein can be combined with high-throughput, automated screening methods to detect activity of cloned, mutagenized polypeptides in host cells. Mutagenized DNA molecules that encode active polypeptides can be recovered from the host cells and rapidly sequenced using modern equipment. These methods allow the rapid determination of the importance of individual amino acid residues in a polypeptide of interest, and can be applied to polypeptides of unknown structure.

The zlipo1 polypeptides of the present invention, including full-length polypeptides, biologically active fragments, and fusion polypeptides, can be produced in genetically engineered host cells according to conventional techniques. Suitable host cells are those cell types that can be transformed or transfected with exogenous DNA and grown in culture, and include bacteria, fungal cells, and cultured higher eukaryotic cells. Eukaryotic cells, particularly cultured cells of multicellular organisms, are preferred. Techniques for manipulating cloned DNA molecules and introducing exogenous DNA into a variety of host cells are disclosed by Sambrook et al., Molecular Cloning: A Laboratory Manual, 2nd ed., Cold Spring Harbor Laboratory Press, Cold Spring Harbor, N.Y., 1989, and Ausubel et al. eds., Current Protocols in Molecular Biology, John Wiley and Sons, Inc., NY, 1987.

In general, a DNA sequence encoding a zlipo1 polypeptide is operably linked to other genetic elements required for its expression, generally including a transcription promoter and terminator, within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a zlipo1 polypeptide into the secretory pathway of a host cell, a secretory signal sequence (also known as a leader sequence, prepro sequence or pre sequence) is provided in the expression vector. The secretory signal sequence may be that of the zlipo1 polypeptide, or may be derived from another secreted protein (e.g., t-PA) or synthesized de novo. The secretory signal sequence is operably linked to the zlipo1 DNA sequence, i.e., the two sequences are joined in the correct reading frame and positioned to direct the newly synthesized polypeptide into the secretory pathway of the host cell. Secretory signal sequences are commonly positioned 5' to the DNA sequence encoding the polypeptide of interest, although certain secretory signal sequences may be positioned elsewhere in the DNA sequence of interest (see, e.g., Welch et al., U.S. Pat. No. 5,037,743; Holland et al., U.S. Pat. No. 5,143,830).

Alternatively, the secretory signal sequence contained in the polypeptides of the present invention is used to direct other polypeptides into the secretory pathway. The present invention provides for such fusion polypeptides. A signal fusion polypeptide can be made wherein a secretory signal sequence derived from 1–17 of SEQ ID NO:2 is be operably linked to another polypeptide using methods known in the art and disclosed herein. The secretory signal sequence contained in the fusion polypeptides of the present invention is preferably fused amino-terminally to an additional peptide to direct the additional peptide into the secretory pathway. Such constructs have numerous applications known in the art. For example, these novel secretory signal sequence fusion constructs can direct the secretion of an active component of a normally non-secreted protein, such as a receptor. Such fusions may be used in vivo or in vitro to direct peptides through the secretory pathway.

Cultured mammalian cells are suitable hosts within the present invention. Methods for introducing exogenous DNA into mammalian host cells include calcium phosphate-mediated transfection (Wigler et al., Cell 14:725, 1978; Corsaro et al., Somatic Cell Genetics 7:603, 1981: Graham et al., Virology 52:456, 1973), electroporation (Neumann et al., EMBO J. 1:841–845, 1982), DEAE-dextran mediated transfection (Ausubel et al., ibid.), and liposome-mediated transfection (Hawley-Nelson et al., Focus 15:73, 1993; Ciccarone et al., Focus 15:80, 1993), and viral vectors (Miller et al., BioTechniques 7:980–90, 1989; Wang et al., Nature Med. 2:714–716, 1996). The production of recombinant polypeptides in cultured mammalian cells is disclosed, for example, by Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134. Suitable cultured mammalian cells include the COS-1 (ATCC No. CRL 1650), COS-7 (ATCC No. CRL 1651), BHK (ATCC No. CRL 1632), BHK 570 (ATCC No. CRL 10314), 293 (ATCC No. CRL 1573; Graham et al., J. Gen. Virol. 36:59–72, 1977) and Chinese hamster ovary (e.g. CHO-K1; ATCC No. CCL 61) cell lines. Additional suitable cell lines are known in the art and available from public depositories such as the American Type Culture Collection, Rockville, Md. In general, strong transcription promoters are preferred, such as promoters from SV-40 or cytomegalovirus. See, e.g., U.S. Pat. No. 4,956,288. Other suitable promoters include those from metallothionein genes (U.S. Pat. Nos. 4,579,821 and 4,601,978) and the adenovirus major late promoter.

Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." A preferred selectable marker is a gene encoding resistance to the antibiotic neomycin. Selection is carried out in the presence of a neomycin-type drug, such as G-418 or the like. Selection systems can also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A preferred amplifiable selectable marker is dihydrofolate reductase, which confers resistance to methotrexate. Other drug resistance genes (e.g., hygromycin resistance, multi-drug resistance, puromycin acetyltransferase) can also be used. Alternative markers that introduce an altered phenotype, such as green fluorescent protein, or cell surface proteins such as CD4, CD8, Class I MHC, placental alkaline phosphatase may be used to sort transfected cells from untransfected cells by such means as FACS sorting or magnetic bead separation technology.

Other higher eukaryotic cells can also be used as hosts, including plant cells, insect cells and avian cells. The use of *Agrobacterium rhizogenes* as a vector for expressing genes in plant cells has been reviewed by Sinkar et al., *J. Biosci.* (Bangalore) 11:47–58, 1987. Transformation of insect cells and production of foreign polypeptides therein is disclosed by Guarino et al., U.S. Pat. No. 5,162,222; and WIPO publication WO 94/06463. Insect cells can be infected with recombinant baculovirus, commonly derived from *Autographa californica* nuclear polyhedrosis virus (AcNPV). See, King, L. A. and Possee, R. D., *The Baculovirus Expression System: A Laboratory Guide*, London, Chapman & Hall; O'Reilly, D. R. et al., *Baculovirus Expression Vectors: A Laboratory Manual*, New York, Oxford University Press., 1994; and, Richardson, C. D., Ed., *Baculovirus Expression Protocols. Methods in Molecular Biology*, Totowa, N.J., Humana Press, 1995. A second method of making recombinant zlipo1 baculovirus utilizes a transposon-based system described by Luckow (Luckow, V. A, et al., *J Virol* 67:4566–79, 1993). This system, which utilizes transfer vectors, is sold in the Bac-to-Bac™ kit (Life Technologies, Rockville, Md.). This system utilizes a transfer vector, pFastBac1™ (Life Technologies) containing a Tn7 transposon to move the DNA encoding the zlipo1 polypeptide into a baculovirus genome maintained in *E. coli* as a large plasmid called a "bacmid." See, Hill-Perkins, M. S. and Possee, R. D., *J Gen Virol* 71:971–6, 1990; Bonning, B. C. et al., *J Gen Virol* 75:1551–6, 1994; and, Chazenbalk, G. D., and Rapoport, B., *J Biol Chem* 270:1543–9, 1995. In addition, transfer vectors can include an in-frame fusion with DNA encoding an epitope tag at the C- or N-terminus of the expressed zlipo1 polypeptide, for example, a Glu-Glu epitope tag (Grussenmeyer, T. et al., *Proc. Natl. Acad. Sci.* 82:7952–4, 1985). Using a technique known in the art, a transfer vector containing zlipo1 is transformed into *E. Coli*, and screened for bacmids which contain an interrupted lacZ gene indicative of recombinant baculovirus. The bacmid DNA containing the recombinant baculovirus genome is isolated, using common techniques, and used to transfect *Spodoptera frugiperda* cells, e.g. Sf9 cells. Recombinant virus that expresses zlipo1 is subsequently produced. Recombinant viral stocks are made by methods commonly used the art.

The recombinant virus is used to infect host cells, typically a cell line derived from the fall armyworm, *Spodoptera frugiperda*. See, in general, Glick and Pasternak, *Molecular Biotechnology: Principles and Applications of Recombinant DNA*, ASM Press, Washington, D.C., 1994. Another suitable cell line is the High FiveO™ cell line (Invitrogen) derived from *Trichoplusia ni* (U.S. Pat. No. 5,300,435). Commercially available serum-free media are used to grow and maintain the cells. Suitable media are Sf900 II™ (Life Technologies) or ESF 921™ (Expression Systems) for the Sf9 cells; and Ex-cellO405™ (JRH Biosciences, Lenexa, Kans.) or Express FiveO™ (Life Technologies) for the *T. ni* cells. The cells are grown up from an inoculation density of approximately $2-5\times10^5$ cells to a density of $1-2\times10^6$ cells at which time a recombinant viral stock is added at a multiplicity of infection (MOI) of 0.1 to 10, more typically near 3. Procedures used are generally described in available laboratory manuals (King, L. A. and Possee, R. D., ibid.; O'Reilly, D. R. et al., ibid.; Richardson, C. D., ibid.). Subsequent purification of the zlipo1 polypeptide from the like. PEI, DEAE, QAE and Q derivatives are preferred. Exemplary chromatographic media include those media derivatized with phenyl, butyl, or octyl groups, such as Phenyl-Sepharose FF (Pharmacia), Toyopearl butyl 650 (Toso Haas, Montgomeryville, Pa.), Octyl-Sepharose (Pharmacia) and the like; or polyacrylic resins, such as Amberchrom CG 71 (Toso Haas) and the like. Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of proteins by amino groups, carboxyl groups, sulfhydryl groups, hydroxyl groups and/or carbohydrate moieties. Examples of coupling chemistries include cyanogen bromide activation, N-hydroxysuccinimide activation, epoxide activation, sulfhydryl activation, hydrazide activation, and carboxyl and amino derivatives for carbodiimide coupling chemistries. These and other solid media are well known and widely used in the art, and are available from commercial suppliers. Methods for binding receptor polypeptides to support media are well known in the art. Selection of a particular method is a matter of routine design and is determined in part by the properties of the chosen support. See, for example, *Affinity Chromatography: Principles & Methods*, Pharmacia LKB Biotechnology, Uppsala, Sweden, 1988.

The polypeptides of the present invention can be isolated by exploitation of for example, their ligand-binding or complex forming properties. For example, affinity chromatography using retinoids can used to bind zlipo1 to the retinoids (Ferrari et al., *FEBS Lett.* 401:73–77, 1997).

Alternatively, immobilized metal ion adsorption (IMAC) chromatography can be used to purify histidine-rich proteins, including those comprising polyhistidine tags. supernatant can be achieved using methods described herein.

Fungal cells, including yeast cells, can also be used within the present invention. Yeast species of particular interest in this regard include *Saccharomyces cerevisiae, Pichia pastoris,* and *Pichia methanolica*. Methods for transforming *S. cerevisiae* cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075. Transformed cells are selected by phenotype determined by the selectable marker, commonly drug resistance or the ability to grow in the absence of a particular nutrient (e.g., leucine). A preferred vector system for use in *Saccharomyces cerevisiae* is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092), and alcohol dehydrogenase genes. See also U.S. Pat. Nos. 4,990,446; 5,063,154; 5,139,936 and 4,661,454. Transformation systems for other yeasts, including *Hansenula polymorpha, Schizosaccharomyces pombe, Kluyveromyces lactis, Kluyveromyces fragilis, Ustilago maydis, Pichia pastoris, Pichia methanolica, Pichia guillermondii* and *Candida maltosa* are known in the art. See, for example, Gleeson et al., *J. Gen. Microbiol.* 132:3459–3465, 1986 and Cregg, U.S. Pat. No. 4,882,279. Aspergillus cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming Neurospora are disclosed by Lambowitz, U.S. Pat. No. 4,486,533.

The use of *Pichia methanolica* as host for the production of recombinant proteins is disclosed in WIPO Publications WO 97/17450, WO 97/17451, WO 98/02536, and WO 98/02565. DNA molecules for use in transforming *P. methanolica* will commonly be prepared as double-stranded, circular plasmids, which are preferably linearized prior to transformation. For polypeptide production in *P. methanolica*, it is preferred that the promoter and terminator in the plasmid be that of a *P. methanolica* gene, such as a *P. methanolica* alcohol utilization gene (AUG1 or AUG2). Other useful promoters include those of the dihydroxyacetone synthase (DHAS), formate dehydrogenase (FMD), and catalase (CAT) genes. To facilitate integration of the DNA into the host chromosome, it is preferred to have the entire expression segment of the plasmid flanked at both ends by host DNA sequences. A preferred selectable marker for use in *Pichia methanolica* is a *P. methanolica* ADE2 gene, which encodes phosphoribosyl-5-aminoimidazole carboxylase (AIRC; EC 4.1.1.21), which allows ade2 host cells to grow in the absence of adenine. For large-scale, industrial processes where it is desirable to minimize the use of methanol, it is preferred to use host cells in which both methanol utilization genes (AUG1 and AUG2) are deleted. For production of secreted proteins, host cells deficient in vacuolar protease genes (PEP4 and PRB1) are preferred. Electroporation is used to facilitate the introduction of a plasmid containing DNA encoding a polypeptide of interest into *P. methanolica* cells. It is preferred to transform *P. methanolica* cells by electroporation using an exponentially decaying, pulsed electric field having a field strength of from 2.5 to 4.5 kV/cm, preferably about 3.75 kV/cm, and a time constant ($\tau$) of from 1 to 40 milliseconds, most preferably about 20 milliseconds.

Prokaryotic host cells, including strains of the bacteria *Escherichia coli*, Bacillus and other genera are also useful host cells within the present invention. Techniques for transforming these hosts and expressing foreign DNA sequences cloned therein are well known in the art (see, e.g., Sambrook et al., ibid.). When expressing a zlipo1 polypeptide in bacteria such as *E. coli,* the polypeptide may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate or urea. The denatured polypeptide can then be refolded and dimerized by diluting the denaturant, such as by dialysis against a solution of urea and a combination of reduced and oxidized glutathione, followed by dialysis against a buffered saline solution. In the latter case, the polypeptide can be recovered from the periplasmic space in a soluble and functional form by disrupting the cells (by, for example, sonication or osmotic shock) to release the contents of the periplasmic space and recovering the protein, thereby obviating the need for denaturation and refolding.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell. *P. methanolica* cells are cultured in a medium comprising adequate sources of carbon, nitrogen and trace nutrients at a temperature of about 25° C. to 35° C. Liquid cultures are provided with sufficient aeration by conventional means, such as shaking of small flasks or sparging of fermentors. A preferred culture medium for *P. methanolica* is YEPD (2% D-glucose, 2% Bacto™ Peptone (Difco Laboratories, Detroit, Mich., 1% Bacto™ yeast extract (Difco Laboratories), 0.004% adenine and 0.006% L-leucine).

It is preferred to purify the polypeptides of the present invention to $\geq 80\%$ purity, more preferably to $\geq 90\%$ purity, even more preferably $\geq 95\%$ purity, and particularly preferred is a pharmaceutically pure state, that is greater than 99.9% pure with respect to contaminating macromolecules, particularly other proteins and nucleic acids, and free of infectious and pyrogenic agents. Preferably, a purified polypeptide is substantially free of other polypeptides, particularly other polypeptides of animal origin.

Expressed recombinant zlipo1 polypeptides (or chimeric zlipo1 polypeptides) can be purified using fractionation and/or conventional purification methods and media. Ammonium sulfate precipitation and acid or chaotrope extraction may be used for fractionation of samples. Exemplary purification steps may include hydroxyapatite, size exclusion, FPLC and reverse-phase high performance liquid chromatography. Suitable chromatographic media include derivatized dextrans, agarose, cellulose, polyacrylamide, specialty silicas, and Briefly, a gel is first charged with divalent metal ions to form a chelate (Sulkowski, *Trends in Biochem.* 3:1–7, 1985). Histidine-rich proteins will be adsorbed to this matrix with differing affinities, depending upon the metal ion used, and will be eluted by competitive elution, lowering the pH, or use of strong chelating agents. Other methods of purification include purification of glycosylated proteins by lectin affinity chromatography and ion exchange chromatography (*Methods in Enzymol.*, Vol. 182, "Guide to Protein Purification", M. Deutscher, (ed.), Acad. Press, San Diego, 1990, pp.529–39). Within additional embodiments of the invention, a fusion of the polypeptide of interest and an affinity tag (e.g.,maltose-binding protein, an immunoglobulin domain) may be constructed to facilitate purification.

Moreover, using methods described in the art, polypeptide fusions, or hybrid zlipo1 proteins, are constructed using regions or domains of the zlipo1 in combination with those of other human lipocalin family proteins, or heterologous proteins (Sambrook et al., ibid., Altschul et al., ibid., Picard, *Cur. Opin. Biology*, 5:511–5, 1994, and references therein). These methods allow the determination of the biological importance of larger domains or regions in a polypeptide of interest. Such hybrids may alter reaction kinetics, binding, constrict or expand the substrate specificity, or alter tissue and cellular localization of a polypeptide, and can be applied to polypeptides of unknown structure.

Fusion proteins can be prepared by methods known to those skilled in the art by preparing each component of the fusion protein and chemically conjugating them. Alternatively, a polynucleotide encoding both components of the fusion protein in the proper reading frame can be generated using known techniques and expressed by the methods described herein. For example, part or all of a domain(s) conferring a biological function may be swapped between zlipo1 of the present invention with the functionally equivalent domain(s) from another family member, such as Von Ebner's gland protein or epididymal-retinoic acid binding protein. Such domains include, but are not limited to, the secretory signal sequence, conserved motifs (e.g., beta strands, helices, and alpha helices) and corresponding structures in the other members of the lipocalin family. Such fusion proteins would be expected to have a biological functional profile that is the same or similar to polypeptides of the present invention or other known lipocalin family proteins, depending on the fusion constructed. Moreover, such fusion proteins may exhibit other properties as disclosed herein.

zlipo1 polypeptides or fragments thereof may also be prepared through chemical synthesis, for example as described by Merrifield, *J. Am. Chem. Soc.* 85:2149, 1963; Stewart et al., "Solid Phase Peptide Synthesis" (2nd Edition), (Pierce Chemical Co., Rockford, Ill., 1984) and Bayer & Rapp Chem. Pept. Prot. 3:3 (1986); and Atherton et al., Solid Phase Peptide Synthesis: *A Practical Approach*, IRL Press, Oxford, 1989. zlipo1 polypeptides may be monomers or multimers; glycosylated or non-glycosylated; pegylated or non-pegylated; and may or may not include an initial methionine amino acid residue.

Proteins of the present invention are useful for their antimicrobial properties. Antimicrobial activity can be measured in vitro using cultured cells or in vivo by administering molecules of the claimed invention to the appropriate animal model. Assays for testing antimicrobial activity are specific to the microbe and are generally known by those ordinarily skilled in the art. For example, in vivo testing for antimicrobial activity is done by inoculating mice intraperitoneally with pathogenic microorganisms in an appropriate broth. Shortly after inoculation, a composition containing zlipo1 polypeptide is administered and death during the subsequent 7 days is recorded. Generally adminstration is intravenous, subcutaneous, intraperitoneal or by mouth. See, for example, Musiek et al., *Antimicrobial Agents Chemother.* 3:40, 1973, for discussion of in vivo and in vitro testing of antimicrobials.

To test zlipo1 molecules of the present invention for in vivo activity host cells expressing zlipo1 polypeptides can be implanted into appropriate animal models. For instance, mammalian transfected (or co-transfected) expression host cells may be embedded in an alginate environment and injected (implanted) into recipient animals. Alginate-poly-L-lysine microencapsulation, permselective membrane encapsulation and diffusion chambers have been described as a means to entrap transfected mammalian cells or primary mammalian cells. These types of non-immunogenic "encapsulations" or microenvironments permit the transfer of nutrients into the microenvironment, and also permit the diffusion of proteins and other macromolecules secreted or released by the captured cells across the environmental barrier to the recipient animal. Most importantly, the capsules or microenvironments mask and shield the foreign, embedded cells from the recipient animal's immune response. Such microenvironments can extend the life of the injected cells from a few hours or days (naked cells) to several weeks (embedded cells).

Alginate threads provide a simple and quick means for generating embedded cells. The materials needed to generate the alginate threads are readily available and relatively inexpensive. Once made, the alginate threads are relatively strong and durable, both in vitro and, based on data obtained using the threads, in vivo. The alginate threads are easily manipulable and the methodology is scalable for preparation of numerous threads. In an exemplary procedure, 3% alginate is prepared in sterile $H_2O$, and sterile filtered. Just prior to preparation of alginate threads, the alginate solution is again filtered. An approximately 50% cell suspension (containing about $5 \times 10^5$ to about $5 \times 10^7$ cells/ml) is mixed with the 3% alginate solution. One ml of the alginate/cell suspension is extruded into a 100 mM sterile filtered $CaCl_2$ solution over a time period of ~15 min, forming a "thread". The extruded thread is then transferred into a solution of 50 mM $CaCl_2$, and then into a solution of 25 mM $CaCl_2$. The thread is then rinsed with deionized water before coating the thread by incubating in a 0.01% solution of poly-L-lysine. Finally, the thread is rinsed with Lactated Ringer's Solution and drawn from solution into a syringe barrel (without needle attached) A large bore needle is then attached to the syringe, and the thread is intraperitoneally injected into a recipient in a minimal volume of the Lactated Ringer's Solution.

An alternative in vivo approach for assaying proteins of the present invention involves viral delivery systems. Exemplary viruses for this purpose include adenovirus, herpesvirus, vaccinia virus and adeno-associated virus (AAV). Adenovirus, a double-stranded DNA virus, is currently the best studied gene transfer vector for delivery of heterologous nucleic acid (for a review, see T. C. Becker et al., *Meth. Cell Biol.* 43:161–89, 1994; and J. T. Douglas and D. T. Curiel, *Science & Medicine* 4:44–53, 1997). The adenovirus system offers several advantages: adenovirus can (i) accommodate relatively large DNA inserts; (ii) be grown to high-titer; (iii) infect a broad range of mammalian cell types; and (iv) be used with a large number of available vectors containing different promoters. Also, because adenoviruses are stable in the bloodstream, they can be administered by intravenous injection. By deleting portions of the adenovirus genome, larger inserts (up to 7 kb) of heterologous DNA can be accommodated. These inserts may be incorporated into the viral DNA by direct ligation or by homologous recombination with a co-transfected plasmid. In an exemplary system, the essential E1 gene has been deleted from the viral vector, and the virus will not replicate unless the E1 gene is provided by the host cell human 293 cell line). When intravenously administered to intact animals, adenovirus primarily targets the liver. If the adenoviral delivery system has an E1 gene deletion, the virus cannot replicate in the host cells. However, the host's tissue (i.e., liver) will express and process (and, if signal sequence is present, secrete) the heterologous protein. Secreted proteins will enter the circulation in the highly vascularized liver, and effects on the infected animal can be determined.

The adenovirus system can also be used for protein production in vitro. By culturing adenovirus-infected non-293 cells under conditions where the cells are not rapidly dividing, the cells can produce proteins for extended periods of time. For instance, BHK cells are grown to confluence in cell factories, then exposed to the adenoviral vector encoding the secreted protein of interest. The cells are then grown under serum-free conditions, which allows infected cells to survive for several weeks without significant cell division. Alternatively, adenovirus vector infected 293 cells can be grown in adherent or suspension cultures at relatively high cell density to produce significant amounts of protein (see Garnier et al., *Cytotechnol.* 15:145–55, 1994). With either protocol, an expressed, secreted heterologous protein can be repeatedly isolated from the cell culture supernatant. Within the infected 293S cell production protocol, non-secreted proteins may also be effectively obtained.

The activity of molecules of the present invention can be measured using a variety of assays that measure the ability to bind small hydrophobic molecules. Such assays include, but are not limited to assays measuring changes in fluorescence intensity (Cogan et al., *Eur. J. Biochem.* 65:71–78, 1976) and equilibrium dialysis of water soluble compounds (Hase et al., *J. Biochem.* 79:373–380, 1976).

In view of the tissue distribution observed for zlipo1, agonists and antagonists have enormous potential in both in vitro and in vivo applications. Compounds identified as zlipo1 agonists, including zlipo1, are useful for transportation of small hydrophobic molecules either in vitro or in vivo. For example, agonist compounds are useful as components of defined cell culture media, to delivery small, hydrophobic molecules to cells and protect them from degradation by enzymes present in serum. Agonists are thus useful in specifically promoting the growth and/or development of testis-specific cell lineages in culture.

zlipo1 can also be used to identify inhibitors (antagonists) of its activity. Test compounds are added to the assays disclosed herein to identify compounds that inhibit the activity of zlipo1. In addition to those assays disclosed herein, samples can be tested for inhibition of zlipo1 activity within a variety of assays designed to measure receptor binding or the stimulation/inhibition of zlipo1-dependent cellular responses. For example, zlipo1-responsive cell lines can be transfected with a reporter gene construct that is responsive to a zlipo1-stimulated cellular pathway. Reporter gene constructs of this type are known in the art, and will generally comprise a zlipo1-DNA response element operably linked to a gene encoding an assayable protein, such as luciferase. DNA response elements can include, but are not limited to, cyclic AMP response elements (CRE), hormone response elements (HRE) insulin response element (IRE) (Nasrin et al., *Proc. Natl. Acad. Sci. USA* 87:5273–7, 1990) and serum response elements (SRE) (Shaw et al. *Cell* 56: 563–72, 1989). Cyclic AMP response elements are reviewed in Roestler et al., *J. Biol. Chem.* 263 (19):9063–6; 1988 and Habener, *Molec. Endocrinol.* 4 (8):1087–94; 1990. Hormone response elements are reviewed in Beato, *Cell* 56:335–44; 1989. Candidate compounds, solutions, mixtures or extracts are tested for the ability to inhibit the activity of zlipo1 on the target cells as evidenced by a decrease in zlipo1 stimulation of reporter gene expression. Assays of this type will detect compounds that directly block zlipo1 binding to cell-surface receptors, as well as compounds that block processes in the cellular pathway subsequent to receptor-ligand binding. In the alternative, compounds or other samples can be tested for direct blocking of zlipo1 binding to receptor using zlipo1 tagged with a detectable label (e.g., $^{125}$I, biotin, horseradish peroxidase, FITC, and the like). Within assays of this type, the ability of a test sample to inhibit the binding of labeled zlipo1 to the receptor is indicative of inhibitory activity, which can be confirmed through secondary assays. Receptors used within binding assays may be cellular receptors or isolated, immobilized receptors.

A zlipo1 polypeptide can be expressed as a fusion with an immunoglobulin heavy chain constant region, typically an $F_c$ fragment, which contains two constant region domains and lacks the variable region. Methods for preparing such fusions are disclosed in U.S. Pat. Nos. 5,155,027 and 5,567,584. Such fusions are typically secreted as multimeric molecules wherein the Fc portions are disulfide bonded to each other and two non-Ig polypeptides are arrayed in closed proximity to each other. Fusions of this type can be used to affinity purify ligand, in vitro assay tool, and as antagonists. For use in assays, the chimeras are bound to a support via the $F_c$ region and used in an ELISA format.

A zlipo1 ligand-binding polypeptide can also be used for purification of ligand. The polypeptide is immobilized on a solid support, such as beads of agarose, cross-linked agarose, glass, cellulosic resins, silica-based resins, polystyrene, cross-linked polyacrylamide, or like materials that are stable under the conditions of use. Methods for linking polypeptides to solid supports are known in the art, and include amine chemistry, cyanogen bromide activation, N-hydroxysuccinimide activation, epoxide activation, sulfhydryl activation, and hydrazide activation. The resulting medium will generally be configured in the form of a column, and fluids containing ligand are passed through the column one or more times to allow ligand to bind to the receptor polypeptide. The ligand is then eluted using changes in salt concentration, chaotropic agents (guanidine HCl), or pH to disrupt ligand-receptor binding.

An assay system that uses a ligand-binding receptor (or an antibody, one member of a complement/anti-complement pair) or a binding fragment thereof, and a commercially available biosensor instrument (BIAcore, Pharmacia Biosensor, Piscataway, N.J.) may be advantageously employed. Such receptor, antibody, member of a complement/anti-complement pair or fragment is immobilized onto the surface of a receptor chip. Use of this instrument is disclosed by Karlsson, *J. Immunol. Methods* 145:229–40, 1991 and Cunningham and Wells, *J. Mol. Biol.* 234:554–63, 1993. A receptor, antibody, member or fragment is covalently attached, using amine or sulfhydryl chemistry, to dextran fibers that are attached to gold film within the flow cell. A test sample is passed through the cell. If a ligand, epitope, or opposite member of the complement/anti-complement pair is present in the sample, it will bind to the immobilized receptor, antibody or member, respectively, causing a change in the refractive index of the medium, which is detected as a change in surface plasmon resonance of the gold film. This system allows the determination of on- and off-rates, from which binding affinity can be calculated, and assessment of stoichiometry of binding.

Figure 2D:
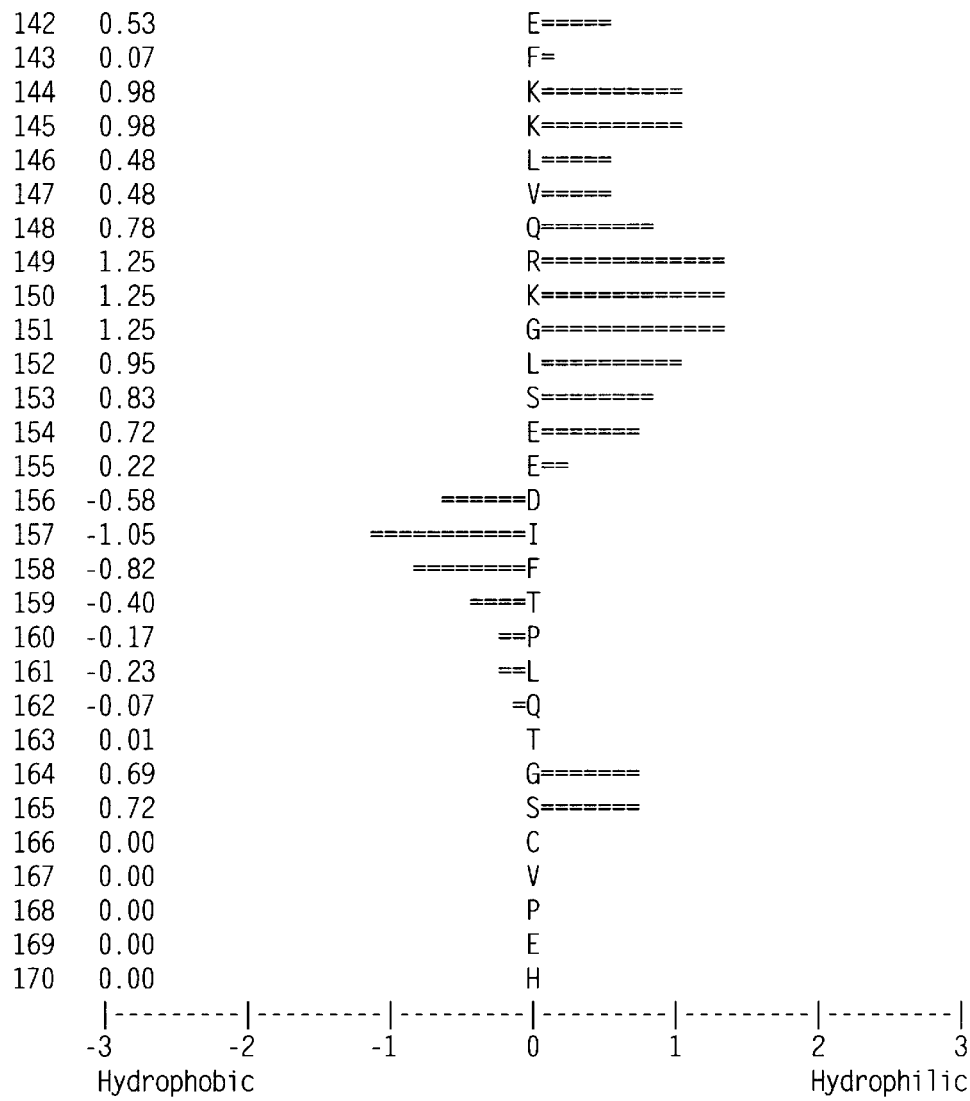

Ligand-binding receptor polypeptides can also be used within other assay systems known in the art. Such systems include Scatchard analysis for determination of binding affinity (see Scatchard, *Ann. NY Acad. Sci.* 51: 660–72, 1949) and calorimetric assays (Cunningham et al., *Science* 253:545–48, 1991; Cunningham et al., *Science* 245:821–25, 1991).

zlipo1 polypeptides can also be used to prepare antibodies that specifically bind to zlipo1 epitopes, peptides or polypeptides. The zlipo1 polypeptide or a fragment thereof serves as an antigen (immunogen) to inoculate an animal and elicit an immune response. Hydrophilicity can be determined, as shown in FIG. 2. Hydrophilicity can be used to determine regions that have the most antigenic potential. Suitable antigens would be the zlipo1 polypeptide encoded by SEQ ID NO:2 from amino acid number 42 (Glu) to amino acid number 47 (Arg), amino acid residue 41 (Pro) to amino acid residue 46 (Pro), amino acid residue 82 (Arg) to amino acid residue 87 (Pro), amino acid residue 81 (Met) to amino acid residue 86 (Glu), amino acid residue 103 (Glu) to amino acid residue 108 (Asp) or a contiguous 9 to 170 amino acid fragment thereof. Antibodies generated from this immune response can be isolated and purified as described herein. Methods for preparing and isolating polyclonal and monoclonal antibodies are well known in the art. See, for example, *Current Protocols in Immunology,* Cooligan, et al. (eds.), National Institutes of Health, John Wiley and Sons, Inc., 1995; Sambrook et al., *Molecular Cloning: A Laboratory Manual, Second Edition,* Cold Spring Harbor, N.Y., 1989; and Hurrell, J. G. R., Ed., *Monoclonal Hybridoma Antibodies: Techniques and Applications,* CRC Press, Inc., Boca Raton, Fla., 1982.

As would be evident to one of ordinary skill in the art, polyclonal antibodies can be generated from a variety of warm-blooded animals, such as horses, cows, goats, sheep, dogs, chickens, rabbits, mice, and rats with a zlipo1 polypeptide or a fragment thereof.

The immunogenicity of a zlipo1 polypeptide may be increased through the use of an adjuvant, such as alum (aluminum hydroxide) or Freund's complete or incomplete adjuvant. Polypeptides useful for immunization also include fusion polypeptides, such as fusions of zlipo1 or a portion thereof with an immunoglobulin polypeptide or with maltose binding protein. The polypeptide immunogen may be a full-length molecule or a portion thereof. If the polypeptide portion is "hapten-like", such portion may be advantageously joined or linked to a macromolecular carrier (such as keyhole limpet hemocyanin (KLH), bovine serum albumin (BSA) or tetanus toxoid) for immunization.

As used herein, the term "antibodies" includes polyclonal antibodies, affinity-purified polyclonal antibodies, monoclonal antibodies, and antigen-binding fragments, such as $F(ab')_2$ and Fab proteolytic fragments. Genetically engineered intact antibodies or fragments, such as chimeric antibodies, Fv fragments, single chain antibodies and the like, as well as synthetic antigen-binding peptides and polypeptides, are also included. Non-human antibodies may be humanized by grafting non-human CDRs onto human framework and constant regions, or by incorporating the entire non-human variable domains (optionally "cloaking" them with a human-like surface by replacement of exposed residues, wherein the result is a "veneered" antibody). In some instances, humanized antibodies may retain non-human residues within the human variable region framework domains to enhance proper binding characteristics. Through humanizing antibodies, biological half-life may be increased, and the potential for adverse immune reactions upon administration to humans is reduced.

Alternative techniques for generating or selecting antibodies useful herein include in vitro exposure of lymphocytes to zlipo1 protein or peptide, and selection of antibody display libraries in phage or similar vectors (for instance, through use of immobilized or labeled zlipo1 protein or peptide. Genes encoding polypeptides having potential zlipo1 polypeptide binding domains can be obtained by screening random peptide libraries displayed on phage (phage display) or on bacteria, such as *E. coli.* Nucleotide sequences encoding the polypeptides can be obtained in a number of ways, such as through random mutagenesis and random polynucleotide synthesis. These random peptide display libraries can be used to screen for peptides which interact with a known target which can be a protein or polypeptide, such as a ligand or receptor, a biological or synthetic macromolecule, or organic or inorganic substances. Techniques for creating and screening such random peptide display libraries are known in the art (Ladner et al., U.S. Pat. No. 5,223,409; Ladner et al., U.S. Pat. No. 4,946,778; Ladner et al., U.S. Pat. No. 5,403,484 and Ladner et al., U.S. Pat. No. 5,571,698) and random peptide display libraries and kits for screening such libraries are available commercially, for instance from Clontech (Palo Alto, Calif.), Invitrogen Inc. (San Diego, Calif.), New England Biolabs, Inc. (Beverly, Mass.) and Pharmacia LKB Biotechnology Inc. (Piscataway, N.J.). Random peptide display libraries can be screened using the zlipo1 sequences disclosed herein to identify proteins which bind to zlipo1. These "binding proteins" which interact with zlipo1 polypeptides can be used for tagging cells; for isolating homolog polypeptides by affinity purification; they can be directly or indirectly conjugated to drugs, toxins, radionuclides and the like. These binding proteins can also be used in analytical methods such as for screening expression libraries and neutralizing activity. The binding proteins can also be used for diagnostic assays for determining circulating levels of polypeptides; for detecting or quantitating soluble polypeptides as marker of underlying pathology or disease. These binding proteins can also act as zlipo1 "antagonists" to block zlipo1 binding and signal transduction in vitro and in vivo.

Antibodies are determined to be specifically binding if: 1) they exhibit a threshold level of binding activity, and/or 2) they do not significantly cross-react with related polypeptide molecules. First, antibodies herein specifically bind if they bind to a zlipo1 polypeptide, peptide or epitope with a binding affinity ($K_a$) of $10^6$ $M^{-1}$ or greater, preferably $10^7$ $M^{-1}$ or greater, more preferably $10^8$ $M^{-1}$ or greater, and most preferably $10^9$ $M^{-1}$ or greater. The binding affinity of an antibody can be readily determined by one of ordinary skill in the art (Scatchard, G., *Ann. NY Acad. Sci.* 51: 660–672, 1949).

A variety of assays known to those skilled in the art can be utilized to detect antibodies which specifically bind to zlipo1 proteins or peptides. Exemplary assays are described in detail in *Antibodies: A Laboratory Manual,* Harlow and Lane (Eds.), Cold Spring Harbor Laboratory Press, 1988. Representative examples of such assays include: concurrent immunoelectrophoresis, radioimmunoassay, radioimmunoprecipitation, enzyme-linked immunosorbent assay (ELISA), dot blot or Western blot assay, inhibition or competition assay, and sandwich assay. In addition, antibodies can be screened for binding to wild-type versus mutant zlipo1 protein or polypeptide.

Antibodies to zlipo1 may be used for tagging cells that express zlipo1; for isolating zlipo1 by affinity purification; for diagnostic assays for determining circulating levels of zlipo1 polypeptides; for detecting or quantitating soluble zlipo1 as marker of underlying pathology or disease; in analytical methods employing FACS; for screening expression libraries; for generating anti-idiotypic antibodies; and as neutralizing antibodies or as antagonists to block zlipo1 in vitro and in vivo. Suitable direct tags or labels include radionuclides, enzymes, substrates, cofactors, inhibitors, fluorescent markers, chemiluminescent markers, magnetic particles and the like; indirect tags or labels may feature use of biotin-avidin or other complement/anti-complement pairs as intermediates. Antibodies herein may also be directly or indirectly conjugated to drugs, toxins, radionuclides and the like, and these conjugates used for in vivo diagnostic or therapeutic applications. Moreover, antibodies to zlipo1 or fragments thereof may be used in vitro to detect denatured zlipo1 or fragments thereof in assays, for example, Western Blots or other assays known in the art.

Antibodies or polypeptides herein can also be directly or indirectly conjugated to drugs, toxins, radionuclides and the like, and these conjugates used for in vivo diagnostic or therapeutic applications. For instance, polypeptides or antibodies of the present invention can be used to identify or treat tissues or organs that express a corresponding anti-complementary molecule (receptor or antigen, respectively, for instance). More specifically, zlipo1 polypeptides or anti-zlipo1 antibodies, or bioactive fragments or portions thereof, can be coupled to detectable or cytotoxic molecules and delivered to a mammal having cells, tissues or organs that express the anti-complementary molecule.

Suitable detectable molecules may be directly or indirectly attached to the polypeptide or antibody, and include radionuclides, enzymes, substrates, cofactors, inhibitors, fluorescent markers, chemiluminescent markers, magnetic particles and the like. Suitable cytotoxic molecules may be directly or indirectly attached to the polypeptide or antibody, and include bacterial or plant toxins (for instance, diphtheria toxin, Pseudomonas exotoxin, ricin, abrin and the like), as well as therapeutic radionuclides, such as iodine-131, rhenium-188 or yttrium-90 (either directly attached to the polypeptide or antibody, or indirectly attached through means of a chelating moiety, for instance). Polypeptides or antibodies may also be conjugated to cytotoxic drugs, such as adriamycin. For indirect attachment of a detectable or cytotoxic molecule, the detectable or cytotoxic molecule can be conjugated with a member of a complementary/anticomplementary pair, where the other member is bound to the polypeptide or antibody portion. For these purposes, biotin/streptavidin is an exemplary complementary/anticomplementary pair.

In another embodiment, polypeptide-toxin fusion proteins or antibody-toxin fusion proteins can be used for targeted cell or tissue inhibition or ablation (for instance, to treat cancer cells or tissues). Alternatively, if the polypeptide has multiple functional domains (i.e., an activation domain or a ligand binding domain, plus a targeting domain), a fusion protein including only the targeting domain may be suitable for directing a detectable molecule, a cytotoxic molecule or a complementary molecule to a cell or tissue type of interest. In instances where the domain only fusion protein includes a complementary molecule, the anti-complementary molecule can be conjugated to a detectable or cytotoxic molecule. Such domain-complementary molecule fusion proteins thus represent a generic targeting vehicle for cell/tissue-specific delivery of generic anti-complementary-detectable/ cytotoxic molecule conjugates.

In another embodiment, zlipo1-cytokine fusion proteins or antibody-cytokine fusion proteins can be used for enhancing in vivo killing of target tissues (for example, blood and bone marrow cancers), if the zlipo1 polypeptide or anti-zlipo1 antibody targets the hyperproliferative blood or bone marrow cell See, generally, Hornick et al., *Blood* 89:4437–47, 1997, wherein is described fusion proteins targeting a cytokine to a desired site of action, thereby providing an elevated local concentration of cytokine. Suitable zlipo1 polypeptides or anti-zlipo1 antibodies target an undesirable cell or tissue (i.e., a tumor or a leukemia), and the fused cytokine mediated improved target cell lysis by effector cells. Suitable cytokines for this purpose include interleukin 2 and granulocyte-macrophage colony-stimulating factor (GM-CSF), for instance.

The bioactive polypeptide or antibody conjugates described herein can be delivered intravenously, intraarterially or intraductally, or may be introduced locally at the intended site of action.

Uses of Polynucleotide/Polypeptide:

Molecules of the present invention can be used to identify and isolate receptors involved in forming a ligand-receptor complex with zlipo1. For example, proteins and peptides of the present invention can be immobilized on a column and membrane preparations run over the column (*Immobilized Affinity Ligand Techniques,* Hermanson et al., eds., Academic Press, San Diego, Calif., 1992, pp.195–202). Proteins and peptides can also be radiolabeled (*Methods in Enzymol.,* vol. 182, "Guide to Protein Purification", M. Deutscher, ed., Acad. Press, San Diego, 1990, 721–737) or photoaffinity labeled (Brunner et al., *Ann. Rev. Biochem.* 62:483–514, 1993 and Fedan et al., *Biochem. Pharmacol.* 33:1167–1180, 1984) and specific cell-surface proteins can be identified.

Other utilities for molecules of the present invention include: as a delivery system to transport and/or stabilize small lipophilic molecules. For example, molecules of the present invention can be used to microencapsulate a small lipophilic molecule that in an active pharmacological agent, and thus protect the agent from extreme pH in the gut, exposure to powerful digestive enzymes and impermeability of gastrointestinal membranes to the active ingredient. Other advantages as encapsulation of the pharmacologic agent can include; preventing premature activation of the agent or protection from gastric irritants.

Molecules of the present invention can be used for binding small fatty acids in blood or tissues to modulate their biological function. Molecules of the present invention can be used to transport retinoids or steroids to receptors, in particular as part of the therapy for breast cancer, emphysema and diseases of the skin and play and important role in reproduction. Other uses include modulation of anti-inflammatory responses (Flower, ibid. 1996), activity as a microbial, either as a enhancer of enzymes (Glasgow, *Arch. Clin. Exp. Opthalmol.* 233:513–522, 1995) or as an enzyme-like molecule itself.

Based on the tissue distribution being restricted to breast tumor (and testis), zlipo1 would have utility as a diagnostic for breast carcinomas and as a tool for predicting tumor aggressiveness.

Polynucleotides encoding zlipo1 polypeptides are useful within gene therapy applications where it is desired to increase or inhibit zlipo1 activity. If a mammal has a mutated or absent zlipo1 gene, the zlipo1 gene can be introduced into the cells of the mammal. In one embodiment, a gene encoding a zlipo1 polypeptide is introduced in vivo in a viral vector. Such vectors include an attenuated or defective DNA virus, such as, but not limited to, herpes simplex virus (HSV), papillomavirus, Epstein Barr virus (EBV), adenovirus, adeno-associated virus (AAV), and the like. Defective viruses, which entirely or almost entirely lack viral genes, are preferred. A defective virus is not infective after introduction into a cell. Use of defective viral vectors allows for administration to cells in a specific, localized area, without concern that the vector can infect other cells. Examples of particular vectors include, but are not limited to, a defective herpes simplex virus 1 (HSV1) vector (Kaplitt et al., *Molec. Cell. Neurosci.* 2:320–30, 1991); an attenuated adenovirus vector, such as the vector described by Stratford-Perricaudet et al., *J. Clin. Invest.* 90:626–30, 1992; and a defective adeno-associated virus vector (Samulski et al., *J. Virol.* 61:3096–101, 1987; Samulski et al., *J. Virol.* 63:3822–8, 1989).

In another embodiment, a zlipo1 gene can be introduced in a retroviral vector, e.g., as described in Anderson et al., U.S. Pat. No. 5,399,346; Mann et al. *Cell* 33:153, 1983; Temin et al., U.S. Pat. No. 4,650,764; Temin et al., U.S. Pat. No. 4,980,289; Markowitz et al., *J. Virol.* 62:1120, 1988; Temin et al., U.S. Pat. No. 5,124,263; International Pat. Publication No. WO 95/07358, published Mar. 16, 1995 by Dougherty et al.; and Kuo et al., *Blood* 82:845, 1993. Alternatively, the vector can be introduced by lipofection in vivo using liposomes. Synthetic cationic lipids can be used to prepare liposomes for in vivo transfection of a gene encoding a marker (Feigner et al., *Proc. Natl. Acad. Sci. USA* 84:7413–7, 1987; Mackey et al., *Proc. Natl. Acad. Sci. USA* 85:8027–31, 1988). The use of lipofection to introduce exogenous genes into specific organs in vivo has certain practical advantages. Molecular targeting of liposomes to specific cells represents one area of benefit. More particularly, directing transfection to particular cells represents one area of benefit. For instance, directing transfection to particular cell types would be particularly advantageous in a tissue with cellular heterogeneity, such as the pancreas, liver, kidney, and brain. Lipids may be chemically coupled to other molecules for the purpose of targeting. Targeted peptides (e.g., hormones or neurotransmitters), proteins such as antibodies, or non-peptide molecules can be coupled to liposomes chemically.

It is possible to remove the target cells from the body; to introduce the vector as a naked DNA plasmid; and then to re-implant the transformed cells into the body. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun or use of a DNA vector transporter. See, e.g., Wu et al., *J. Biol. Chem.* 267:963–7, 1992; Wu et al., *J. Biol. Chem.* 263:14621–4, 1988.

Antisense methodology can be used to inhibit zlipo1 gene transcription, such as to inhibit cell proliferation in vivo. Polynucleotides that are complementary to a segment of a zlipo1-encoding polynucleotide (e.g., a polynucleotide as set froth in SEQ ID NO:1) are designed to bind to zlipo1-encoding mRNA and to inhibit translation of such mRNA. Such antisense polynucleotides are used to inhibit expression of zlipo1 polypeptide-encoding genes in cell culture or in a subject.

Transgenic mice, engineered to express the zlipo1 gene, and mice that exhibit a complete absence of zlipo1 gene function, referred to as "knockout mice" (Snouwaert et al., *Science* 257:1083, 1992), may also be generated (Lowell et al., *Nature* 366:740–42, 1993). These mice may be employed to study the zlipo1 gene and the protein encoded thereby in an in vivo system.

Radiation hybrid mapping is a somatic cell genetic technique developed for constructing high-resolution, contiguous maps of mammalian chromosomes (Cox et al., *Science* 250:245–50, 1990). Partial or full knowledge of a gene's sequence allows one to design PCR primers suitable for use with chromosomal radiation hybrid mapping panels. Radiation hybrid mapping panels are commercially available which cover the entire human genome, such as the Stanford G3 RH Panel and the GeneBridge 4 RH Panel (Research Genetics, Inc., Huntsville, Ala.). These panels enable rapid, PCR-based chromosomal localizations and ordering of genes, sequence-tagged sites (STSs), and other nonpolymorphic and polymorphic markers within a region of interest. This includes establishing directly proportional physical distances between newly discovered genes of interest and previously mapped markers. The precise knowledge of a gene's position can be useful for a number of purposes, including: 1) determining if a sequence is part of an existing contig and obtaining additional surrounding genetic sequences in various forms, such as YACs, BACs or cDNA clones; 2) providing a possible candidate gene for an inheritable disease which shows linkage to the same chromosomal region; and 3) cross-referencing model organisms, such as mouse, which may aid in determining what function a particular gene might have.

Sequence tagged sites (STSs) can also be used independently for chromosomal localization. An STS is a DNA sequence that is unique in the human genome and can be used as a reference point for a particular chromosome or region of a chromosome. An STS is defined by a pair of oligonucleotide primers that are used in a polymerase chain reaction to specifically detect this site in the presence of all other genomic sequences. Since STSs are based solely on DNA sequence they can be completely described within an electronic database, for example, Database of Sequence Tagged Sites (dbSTS), GenBank, (National Center for Biological Information, National Institutes of Health, Bethesda, Md. http://www.ncbi.nlm.nih.gov), and can be searched with a gene sequence of interest for the mapping data contained within these short genomic landmark STS sequences. For pharmaceutical use, the proteins of the present invention are formulated for parenteral, particularly intravenous or subcutaneous, delivery according to conventional methods. Intravenous administration will be by bolus injection or infusion over a typical period of one to several hours. In general, pharmaceutical formulations will include a zlipo1 protein in combination with a pharmaceutically acceptable vehicle, such as saline, buffered saline, 5% dextrose in water or the like. Formulations may further include one or more excipients, preservatives, solubilizers, buffering agents, albumin to prevent protein loss on vial surfaces, etc. Methods of formulation are well known in the art and are disclosed, for example, in Remington: *The Science and Practice of Pharmacy*, Gennaro, ed., Mack Publishing Co., Easton, Pa., 19th ed., 1995. Therapeutic doses will generally be in the range of 0.1 to 100 μg/kg of patient weight per day, preferably 0.5–20 μg/kg per day, with the exact dose determined by the clinician according to accepted standards, taking into account the nature and severity of the condition to be treated, patient traits, etc. Determination of dose is within the level of ordinary skill in the art. The proteins may be administered for acute treatment, over one week or less, often over a period of one to three days or may be used in chronic treatment, over several months or years.

The invention is further illustrated by the following non-limiting examples.

EXAMPLE 1

Scanning of a translated DNA database using von Ebner's gland protein as a query resulted in identification of an expressed sequence tag (EST) sequence found to be homologous to positions 7–192 of the zlipo1 cDNA sequence, as shown in SEQ ID NO: 1, and designated zlipo1.

The DNA sequence for zlipo1 was determined from cDNA clones corresponding to the EST identified. A 600 bp insert was isolated and used as a probe for Northern analysis.

EXAMPLE 2

Northerns were performed using Human Multiple Tissue Blots from Clontech (Palo Alto, Calif.). The 600 bp DNA fragment described in Example 1 was electrophoresed on a 1% agarose gel, the fragment was electroeluted, and then radioactively labeled using a radon priming MULTIPRIME DNA labeling system (Amersham, Arlington Heights, Ill.) according to the manufacturer's specifications. The probe was purified using a NUCTRAP push column (Stratagene Cloning Systems, La Jolla, Calif.). EXPRESSHYB (Clontech, Palo Alto, Calif.) solution was used for prehybridization and as a hybrizing solution for the Northern blots. Hybridization took place overnight at 65° C., and the blots were then washed 4 times in 2× SSC and 0.05% SDS at RT, followed by two washes in 0.1× SSC and 0.1% SDS at 50° C. A single transcript was observed at 0.8 kb, in testis only.

EXAMPLE 3

Zlipo1 was mapped to chromosome 9 using the commercially available "GeneBridge 4 Radiation Hybrid Panel" (Research Genetics, Inc., Huntsville, Ala.). The GeneBridge 4 Radiation Hybrid Panel contains DNAs from each of 93 radiation hybrid clones, plus two control DNAs (the HFL donor and the A23 recipient). A publicly available WWW server (http://www-genome.wi.mit.edu/cgi-bin/contig/rhmapper.pl) allows mapping relative to the Whitehead Institute/MIT Center for Genome Research's radiation hybrid map of the human genome (the "WICGR" radiation hybrid map) which was constructed with the GeneBridge 4 Radiation Hybrid Panel.

For the mapping of zlipo1 with the "GeneBridge 4 RH Panel", 25 μl reactions were set up in a 96-well microtiter plate (Stratagene, La Jolla, Calif.) and used in a "RoboCycler Gradient 96" thermal cycler (Stratagene). Each of the 95 PCR reactions consisted of 2.5 μl "10× KlenTaq reaction buffer" (Clontech Laboratories, Inc., Palo Alto, Calif.), 2 μl dNTPs mix (2.5 mM each, Perkin-Elmer, Foster City, Calif.), 1.25 μl sense primer, ZC 13,139, (SEQ ID NO: 3), 1.25 μl antisense primer, ZC 13,137, (SEQ ID NO: 4), 2.5 μl "RediLoad" (Research Genetics, Inc., Huntsville, Ala.), 0.5 μl "50× Advantage KlenTaq Polymerase Mix" (Clontech Laboratories, Inc.), 25 ng of DNA from an individual hybrid clone or control and ddH2O for a total volume of 25 μl. The reactions were overlaid with an equal amount of mineral oil and sealed. The PCR cycler conditions were as follows: an initial 1 cycle 5 minute denaturation at 95° C., 35 cycles of a 1 minute denaturation at 95° C., 1 minute annealing at 60° C. and 1.5 minute extension at 72° C., followed by a final 1 cycle extension of 7 minutes at 72° C. The reactions were separated by electrophoresis on a 3 % NuSieve GTG agarose gel (FMC Bioproducts, Rockland, Me.).

The results showed that zlipo1 maps to 524.95CR_3000 from the top of the WICGR radiation hybrid map. Proximal and distal framework markers were D95158 and WI-14048, respectively. This positions zlipo1 in the 9q34.3 region of the integrated LDB chromosome 9 map. (The Genetic Location Database, University of Southhampton, WWW server: http:// cedar.genetics. soton.ac.uk/public_html/).

Other members of the lipocalin family, von Ebner's gland protein, have been localized to band q34 of chromosome 9, and it has been postulated that a lipocalin superfamily gene cluster resides within this chromosomal region (Glasgow et al., *Curr. Eye Res.* 12:1019–1023, 1993 and Dewald et al., *Ann. Hum. Genet.* 60(Pt. 4):281–291, 1996).

EXAMPLE 4

In vivo injections of zlipo1 into mice resulted in lower fasting blood glucose levels than mice treated with vehicle alone. Female mice had lower cholesterol than mice treated with vehicle alone.

Male and female mice (CD-1; Harlan Biosciences, Indianapolis, Ind.) were injected subcutaneously with purified human zlipo1 protein for 7 days consecutively. Thirty mice were divided into three groups of 10 (5 males and 5 females) resulting in a group treated with vehicle only, a group treated with 1.0 μg/mouse/day zlipo1, and a group treated with 10.0 μg/mouse/day zlipo1.

Three days prior to injection, the animals were weighed, bled, ear tagged under ether anesthesia. Days 1–7, the animals were injected zlipo1 or vehicle, and clinical observations were made. On day 7, the animals were raised off bedding and fasted overnight. Day 8, the animals were weighted and anesthetized with ether, bled and sacrificed.

During treatment, all animals were healthy, behaved normally and weight gain was comparable between treated and untreated males and females. Male and female animals treated with the high dose of zlipo1 had lower fasting blood glucose levels than vehicle controls on day 8. In addition, the cholestrol levels were reduced in female mice compared to controls.

EXAMPLE 5

A. Mammalian Expression

Mammalian Expression Constructs zlipo1 mammalian expression constructs were prepared in the vector, pZP9, (deposited at the American Type Culture Collection, 12301 Parklawn Drive, Rockville, Md. and designated No. 98668) with either an N-terminal or C-terminal FLAG affinity tag (Sigma, St. Louis, Mo.). The vector used for the N-terminal FLAG tag (designated NFpZP9), contains at the 5' end of the cloning site, a tPA leader followed by the FLAG tag sequence (DYKDDDDK, as shown in SEQ ID NO: 6) and a two amino acid spacer (GS). The Gly, Ser residues of the spacer constitute a BamHI restriction site allowing for insertion of the desired cDNA with no extra residues. The downstream 3' cloning site was Xba1. The zlipo1 sequence was inserted into the BamHI/Xba1 site directionally with the predicted mature end of the protein at the 5' end (as shown in SEQ ID NO: 1 from nucleotide 52 to 516). The Xba 1 site at the 3' end occurs directly after an in-frame stop codon.

The C-terminal FLAG tag construct was made and designated CFpZP9. An Xho1 site at the 5' end of the cloning site was utilized for cloning of the insert. At the 3' end, the vector contains an in-frame spacer (GS) followed by the FLAG tag (SEQ ID NO: 6). The spacer (GS) constitute a BamHI site which allows for insertion of the cDNA of interest with no extra residues. The zlipo1 sequence, containing the native leader sequence was inserted directionally using the Xho1/BamHI site. A stop codon occurs after the final FLAG residue.

cDNA inserts for both the N- and C-terminally tagged constructs were prepared by PCR. Primers encoding the appropriate restriction sites were designed based on the sequence of zlipo1 (SEQ ID NO: 1). Primers ZC13290 (SEQ ID NO: 8) and ZC13291 (SEQ ID NO: 9) were used to prepare the N-terminal Flag tag zlipo1 insert. Primers ZC13270 (SEQ ID NO: 10) and ZC13271 (SEQ ID NO: 11) were used to prepare the C-terminal FLAG tag insert. A fifty microliter PCR reaction was set up for each insert using 30 pmol of the 5' sense primer and 30 pmol of the 3' antisense primer. Four microliters of 10 mM dNTPs were then added along with 0.5 microliters of ExTaq (TaKaRa Shuzo Co. Ltd., Shiga, Japan). Full-length zlipo1 was used as a template for both reactions. A three-step cycle PCR reaction was conducted in a Perkin Elmer 2400 thermal cycler (PE Applied Biosystems, Foster City, Calif.). The reactions were subjected to 35 amplification cycles (30 sec at 95° C., 20 sec at 55° C. and 30 sec at 72° C.) followed by a 10 min extension step at 72° C. The reactions were run on a 2% agarose gel, the bands were excised and purified using the QiaQuick gel extraction kit (Qiagen, Chatsworth, Calif.).

Ligation reactions were prepared using the purified inserts and the pZP9 vector cut with the appropriate restriction enzymes. Electrocompetent DH10B cells (GIBCO-BRL, Gaithersburg, Md.) were transformed after ligation, plated onto LB-Amp plates, and incubated overnight at 37° C. Colonies containing inserts were analyzed by PCR. cDNA from positive colonies was sequenced for PCR errors. Plasmids for both N- and C-terminally FLAG tagged zlipo1 were isolated, and named zlipo1NF/pZP9 and zlipo1CF/pZP9, respectively.

BHK Expression of Zlipo1

BHK 570 cells (ATCC NO: CRL-10314) were plated in 10 cm tissue culture dishes and allowed to grow to approximately 50 to 70% confluency overnight at 37° C., 5% $CO_2$, in DMEM/FBS media (DMEM, GibcoBRL High Glucose, (Gibco BRL), 5% fetal bovine serum (Hyclone, Logan, Utah), 1 μM L-glutamine (JRH Biosciences, Lenexa, Kans.), 1 μM sodium pyruvate (Gibco BRL). The cells were then transfected with the plasmid zlipo1NF/pZP9 (full length N-terminal FLAG tag) or zlipo1CF/pZP9 (full length C-terminal FLAG tag) using Lipofectamine™ (Gibco BRL), in serum free (SF) media formulation (DMEM, 10 mg/ml transferrin, 5 mg/ml insulin, 2 mg/ml fetuin, 1% L-glutamine and 1% sodium pyruvate). Sixteen micrograms of each expression construct were separately diluted into 15 ml tubes to a total final volume of 640 μl with SF media. In separate tubes, 35 μl of Lipofectamine™ (Gibco BRL) was mixed with 605 μl of SF medium. The Lipofectamine™ mix was added to the expression construct mix and allowed to incubate approximately 30 minutes at room temperature. Five milliliters of SF media was added to the DNA:Lipofectamine™ mixture. Three plates of cells were rinsed once with 5 ml of SF media, aspirated, and the DNA:Lipofectamine™ mixture was added. The cells were incubated at 37° C. for five hours, then 6.4 ml of DMEM/10% FBS, 1% PSN media was added to each plate. The plates were incubated at 37° C. overnight and the DNA:Lipofectamine™ mixture was replaced with fresh FBS/DMEM media the next day. On day 2 post-transfection, the cells were split into the selection media (DMEM/FBS media from above with the addition of 1 μM methotrexate (Sigma Chemical Co., St. Louis, Mo.) in 150 mm plates at 1:10, 1:20 and 1:50. The cells were given fresh selection medium at day 5 post-transfection.

Approximately 10–12 days post-transfection, two 150 mm culture dishes of methotrexate resistant colonies were chosen, the media aspirated, the plates washed with 10 ml serum-free ESTEP 2 media (668.7 g/50 L DMEM (GibcoBRL), 5.5 g/50 L pyruvic acid, sodium salt 96% (Mallinckrodt, St. Louis, Mo.), 185.0 g/50 L NaHCO$_3$ (Mallinkrodt), 5.0 mg/ml, 25 ml/50 L insulin, 10.0 mg/ml and 25 ml/50 L transferrin). The wash media was aspirated and replaced with 5 ml serum-free ESTEP 2. Sterile Teflon mesh (Spectrum Medical Industries, Los Angeles, Calif.) pre-soaked in serum-free ESTEP 2 was then placed over the cells. A sterile nitrocellulose filter pre-soaked in serum-free ESTEP 2 was then placed over the mesh. Orientation marks on the nitrocellulose were transferred to the culture dish. The plates were then incubated for 5–6 hours in a 37° C., 5% CO$_2$ incubator. Following incubation, the filter was removed, and the media aspirated and replaced with DMEM/5% FBS, 1× PSN (Gibco BRL) media. The filters were blocked in 2.5% nonfat dry milk/Western A buffer (Western A: 50 mM Tris pH 7.4, 5 mM EDTA, 0.05% NP-40, 150 mM NaCl and 0.25% gelatin) overnight at 4° C. on a rotating shaker. The filter was then incubated with a goat anti-human FLAG-HRP conjugate at a 1:4000 dilution (5 μl antibody in 20 ml buffer) in 2.5% nonfat dry milk/Western A buffer (Western A: 50 mM Tris pH 7.4, 5 mM EDTA, 0.05% NP-40, 150 mM NaCl and 0.25% gelatin) at room temperature for 1 hour on a rotating shaker. The filter was then washed three times at room temperature in PBS plus 0.1% Tween 20, 15 minutes per wash. The filter was developed with ECL reagent (Amersham Corp., Arlington Heights, Ill.) according the manufacturer's directions and exposed to film (Hyperfilm ECL, Amersham) for approximately 5 minutes.

The film was aligned with the plate containing the colonies. Using the film as a guide, suitable colonies were selected. Sterile, 3 mm coloning discs (PGC Scientific Corp., Frederick, Md.) were soaked in trypsin, and placed on the colonies. The colonies were transferred into 200 μl of selection medium in a 96 well plate. A series of seven, two-fold dilutions were carried out for each colony. The 150 mm culture dish was then trypsinized and the remainder of the cells are pooled and split into two T162 flasks containing DMEM/5% FBS and 1 μM MTX media. The cells were grown for one week at 37° C., at which time wells which received the lowest dilution of cells and were at the optimum density were selected, trypsinized and transferred to a 12 well plate containing selection media.

The clones were expanded directly from the 12 well plate to 2 T-75 flasks. One flask from each clone is grown in serum-free ESTEP 2 and the media harvested for Western Blot analysis. Clones of each of the expression constructs, based on Western blot analysis were selected, pooled together and transferred to large scale culture.

Large Scale Mammalian Expression of Zlipo1

One T-162 flask, containing confluent cells expressing zlipo1/NF and one flask containing zlipo1/CF expressing cells, obtained from the expression procedure described above, were expanded into five T-162 flasks. One of the five resulting flasks was used to freeze down four cryovials, and the other four flasks were used to generate a Nunc cell factory (Nunc A/S, Roskilde, DK).

zlipo1/NF and zlipo1/CF were combined and used to seed two Nunc cell factories (10 layers). Briefly, the cells from the T-162 flasks described above were detached using trypsin, pooled, and added to 1.5 liters ESTEP1 media (668.7 g/50 L DMEM (GibcoBRL), 5.5 g/50 L pyruvic acid, sodium salt 96% (Mallinckrodt), 185.0 g/50 L NaHCO$_3$ (Mallinkrodt), 5.0 mg/ml and 25 ml/50 L insulin (JRH Biosciences), 10.0 mg/ml and 25 ml/50 L transferrin (JRH Biosciences), 2.5 L/50 L fetal bovine serum (Hyclone), 1 μM MTX, with pH adjusted to 7.05+/−0.05) prewarmed to 37° C. The media containing the cells was then poured into the Nunc cell factories via a funnel. The cell factories were placed in a 37° C. and 5.0% CO$_2$ incubator.

At 80–100% confluence, a visual contamination test (phenol red color change) was performed on the cell factories. Since no contamination was observed, supernatant from the confluent factories was poured into a small harvest container, sampled and discarded. The adherent cells were then washed once with 400 ml PBS. To detach the cells from the factories, 100 mls of trypsin was added to each and removed and the cells were then incubated for 5 to 10 minutes in the residual trypsin. The cells were collected following two, 200 ml washes of ESTEP1 media. To each of ten ESTEP1 media-containing bottles (1.5 liters each, at 37° C.) was added 40 mls of collected cells. One 1.5 liter bottle was then used to fill one Nunc factory. Each cell factory was placed in a 37° C. and 5.0% CO$_2$ incubator.

At 80–90% confluence, a visual contamination test (phenol red color change) was performed and once lack of contamination was observed, supernatant from the confluent factories was poured into a small harvest container, sampled and discarded. Cells were then washed once with 400 ml PBS. 1.5 liters of ESTEP2 media (668.7 g/50 L DMEM (GibcoBRL), 5.5 g/50 L pyruvic acid, sodium salt 96% (Mallinckrodt), 185.0 g/50 L NaHCO$_3$ (Mallinkrodt), 5.0 mg/ml, 25 ml/50 L insulin, 10.0 mg/ml and 25 ml/50 L transferrin) was added to each cell factory. The cell factories were incubated at 37° C. and 5.0% CO$_2$.

At approximately 40 a check for contamination was done. Supernatant from each factory was poured into small harvest containers. A total of 15 liters was collected from all 10 factories. Fresh serum-free media (1.5 liters) was poured into each Nunc cell factory, and the factories were incubated at 37° C. and 5.0% $CO_2$. One ml of supernatant harvest was transferred to a microscope slide, and subjected to microscopic analysis for contamination. The contents of the small harvest containers for each factory were pooled and immediately filtered.

At 50 hours, second harvest at 50 hours was done, substantially as described above (15 L were obtained), and the cell factories were discarded thereafter. An assembled filter train apparatus was used for aseptic filtration of the harvest supernatant (conditioned media). Assembly was a follows: tubing was wire-tied to an Opti-Cap filter (Millipore Corp., Bedford, Mass.) and a Gelman Supercap 50 filter (Gelman Sciences, Ann Arbor, Mich.). The Supercap 50 filter was also attached to a sterile capped container located in a hood; tubing located upstream of the Millipore Opti-cap filter was inserted into a peristaltic pump; and the free end of the tubing was placed in the large harvest container. The peristaltic pump was run between 200 and 300 rpm, until all of the conditioned media passed through the 0.22 $\mu$m final filter into a sterile collection container. The filtrate was placed in a 4° C. cold room pending purification. The media was concentrated 10× with a Millipore 5 kDA cut off concentrator (Millipore Corp., Bedford, Mass.) according to manufacturer's direction and subjected to Western Blot analysis using an anti-FLAG tag antibody (Kodak).

B. Yeast Expression

Construction of N-Terminal Glu-Glu and FLAG Tagged Yeast Expression Vectors

Expression of zlipo1 in *Pichia methanolica* utilizes the expression system described in commonly-assigned WIPO publication WO 97/17450. An expression plasmid containing all or part of a polynucleotide encoding zlipo1 was constructed via homologous recombination.

An expression vector was built from pCZR190 to express N-terminal FLAG-tagged (NF) zlipo1 polypeptides. The pCZR190 vector contains the AUG1 promoter, followed by the aFpp leader sequence and an amino-terminal peptide tag (FLAG), followed by a blunt-ended Sma I restriction site, a translational STOP codon, followed by the AUG1 terminator, the ADE2 selectable marker, and finally the AUG1 3' untranslated region. Also included in this vector are the URA3 and CEN-ARS sequences required for selection and replication in *S. cerevisiae*, and the AmpR and colE1 ori sequences required for selection and replication in *E. coli*. A second expression vector was built from zCZR191 to express a N-terminal Glu-Glu-tagged (NEE) zlipo1 polypeptides. The zCZR191 expression vector is as described above, having an amino terminal Glu-Glu tag (SEQ ID NO: 7). The zlipo1 sequence inserted into these vectors begins at residue 16 (Leu) as shown in SEQ ID NO: 2.

For each construct two linkers are prepared, and along with zlipo1, were homologously recombined into the yeast expression vectors described herein. The N-terminal FLAG linker (shown in SEQ ID NO: 24) spans 70 base pairs of the alpha factor prepro (aFpp) coding sequence on one end, followed by the FLAG tag and joins it to 70 base pairs of the amino-terminus coding sequence of mature zlipo1 sequence on the other. The NEE-tagged linker joins Glu-Glu tag between the aFpp coding sequence and the zlipo1 sequence. The C-terminal linker spans about 70 base pairs of carboxy terminus coding sequence of zlipo1 on one end with 70 base pairs of AUG1 terminator sequence.

Construction of the NEE-tagged-Zlipo1 Plasmid

An NEE-tagged-zlipo1 plasmid was made by homologously recombining 100 ng of the SmaI digested pCZR191 acceptor vector, 1 mg of BamHI-XbaI zlipo1 cDNA donor fragment, 1 mg NEE-tagged-zlipo1 linker and 1 mg of C-terminal untagged linker in *S. cerevisiae*.

The NEE-zlipo1 linker was synthesized by a PCR reaction. To a final reaction volume of 100 ml was added 1 pmol each of linkers, ZC13,731 (SEQ ID NO: 12) and ZC13,762 (SEQ ID NO: 13), and 100 pmol of each primer ZC13,497 (SEQ ID NO: 14) and ZC13,764 (SEQ ID NO: 15), 10 ml of 10× PCR buffer (Boehringer Mannheim, Indianapolis, Id.), 1 ml Pwo Polymerase (Boehringer Mannheim), 10 ml of 0.25 mM nucleotide triphosphate mix (PE Applied Biosystems) and dH2O. The PCR reaction was run 10 cycles at 30 seconds at 94° C., 1 minute at 50° C. and 1 minute at 72° C., concluded with a 6 minute extension at 72° C. The resulting 141 bp double stranded, NEE-tagged linker is disclosed in SEQ ID NO: 16

The C-terminal untagged zlipo1 linker was made via a PCR reaction as described using oligonucleotides ZC13,734 (SEQ ID NO: 18), ZC13,727 (SEQ ID NO: 19), ZC13,725 (SEQ ID NO: 20) and ZC13,733 (SEQ ID NO: 21). The resulting 147 bp double stranded, C-terminal untagged linker is disclosed in SEQ ID NO: 17.

Construction of the NF-zlipo1 Plasmid

An NF-zlipo1 plasmid was made by homologously recombining 100 ng of Sma I digested pCZR190 acceptor vector, the 1 mg of BamHI-Xba1 zlipo1 cDNA donor fragment, 1 mg of N-terminal FLAG-tagged zlipo1 linker and 1 mg of C-terminal untagged linker in *S. cerevisiae*.

The N-terminal FLAG-tagged zlipo1 linker was made using a PCR reaction, as described above, using oligonucleotides ZC13,497 (SEQ ID NO: 14), ZC13,735 (SEQ ID NO: 22), ZC13,839 (SEQ ID NO: 23) and ZC13,764 (SEQ ID NO: 15). The resulting 141 bp double stranded, N-terminal FLAG-tagged linker is disclosed in SEQ ID NO: 24.

The C-terminal untagged zlipo1 linker was made using a PCR reaction, as described previously, using oligonucleotides ZC13,734 (SEQ ID NO: 18), ZC13,727 (SEQ ID NO: 19), ZC13,725 (SEQ ID NO: 20) and ZC13,733 (SEQ ID NO: 21). The resulting 147 bp double stranded, C-terminal untagged linker is disclosed in SEQ ID NO:. 17

One hundred microliters of competent yeast cells (*S. cerevisiae*) were independently combined with 10 ml of the various DNA mixtures from above and transferred to a 0.2 cm electroporation cuvette. The yeast/DNA mixtures were electropulsed at 0.75 kV (5 kV/cm), o ohms, 25 $\mu$F. To each cuvette was added 600 $\mu$l of 1.2 M sorbitol and the yeast was plated in two 300 $\mu$l aliquots onto two URA-D plates and incubated at 30° C.

After about 48 hours, the Ura+ yeast transformants from a single plate were resuspended in 1 ml $H_2O$ and spun briefly to pellet the yeast cells. The cell pellet was resuspended in 1 ml of lysis buffer (2% Triton X-100, 1% SDS, 100 mM NaCl, 10 mM Tris, pH 8.0, 1 mM EDTA). Five hundred microliters of the lysis mixture was added to an Eppendorf tube containing 300 $\mu$l acid washed glass beads and 200 $\mu$l phenol-chloroform, vortexed for 1 minute intervals two or three times, followed by a 5 minute spin in a Eppendorf centrifuge at maximum speed. Three hundred microliters of the aqueous phase was transferred to a fresh tube, and the DNA precipitated with 600 μl ethanol (EtOH), followed by centrifugation for 10 minutes at 4° C. The DNA pellet was resuspended in 100 μl H$_2$O.

Transformation of electrocompetent *E. coli* cells (DH10B, GibcoBRL) was done with 0.5–2 ml yeast DNA prep and 40 ul of DH10B cells. The cells were electropulsed at 2.0 kV, 25 mF and 400 ohms. Following electroporation, 1 ml SOC (2% Bacto Tryptone (Difco, Detroit, Mich.), 0.5% yeast extract (Difco), 10 mM NaCl, 2.5 mM KCl, 10 mM MgCl2, 10 mM MgSO4, 20 mM glucose) was plated in 250 μl aliquots on four LB AMP plates (LB broth (Lennox), 1.8% Bacto Agar (Difco), 100 mg/L Ampicillin).

Individual clones harboring the correct expression construct for NEE and NF tagged zlipo1 were identified by restriction digest to verify the presence of the zlipo1 insert and to confirm that the various DNA sequences had been joined correctly to one another. The insert of positive clones were subjected to sequence analysis. Larger scale plasmid DNA was isolated using the Qiagen Maxi kit (Qiagen) according to manufacturer's instruction, and the DNA was digested with Not I to liberate the Pichia-Zlipo1 expression cassette from the vector backbone. The Not I-restriction digested DNA fragment was then transformed into the *Pichia methanolica* expression host, PMAD16. This was done by mixing 100 ml of prepared competent PMAD16 cells with 10 mg of Not I restriction digested zlipo1 and transferred to a 0.2 cm electroporation cuvette. The yeast/DNA mixture was electropulsed at 0.75 kV, 25 mF, infinite ohms. To the cuvette was added 1 ml of 1× Yeast Nitrogen Base and 500 ml aliquots were plated onto two ADE DS (0.056% -Ade -Trp -Thr powder, 0.67% yeast nitrogen base without amino acids, 2% D-glucose, 0.5% 200× tryptophan, threonine solution, and 18.22% D-sorbitol) plates for selection and incubated at 30° C. Clones were picked and screened via Western blot for high-level Zlipo1 expression. The resulting NEE-tagged-zlipo1 plasmid containing yeast strain was designated PMAD16::pSDH111.2.7 and the NF-tagged-zlipo1 plasmid containing yeast strain was designated PMAD16::pSDH108.3.6. These resulting strains were fermented.

C. Baculovirus Expression of Zlipo1
Baculovirus Expression Vectors pFSG35 and pFSGE35

Two expression vectors were prepared to express the zlipo1 polypeptides in insect cells, pFLP1, designed to express an untagged zlipo1 polypeptide and pFLPE1, designed to express a zlipo1 polypeptide with a C-terminal Glu-Glu tag (SEQ ID NO:7).

pFLP1

A 535 bp PCR generated zlipo1 DNA fragment was created using ZC13405 (SEQ ID NO:26) and ZC13406 (SEQ ID NO:27) as PCR primers and an uncut PCR fragment as a template. The PCR reaction was incubated at 94° C. for 2 minutes, followed by 30 cycles of 45 seconds at 94° C., 1 minute at 55° C. and 72° C. for 1 minute with a 1 second/cycle segment extension. The resultant PCR product was then run on a 3% gel (2% NuSieve/1% BRL agarose). The 535 bp fragment was captured by diluting 15 fold with 0.1 mM EDTA pH 8.0 and then ligated into the vector pCR2.1 (TA Cloning Kit, Invitrogen Inc., San Diego, Calif.), according to manufacturer's instructions. The resultant clones were screened for the proper insert orientation and sequenced to confirm identity. The resulting clone, pLP1, was digested with Bgl II and Asp718 and the digest run on a 1% SeaPlaque/1% NuSieve agarose gel. A 535 bp band was excised, diluted to 0.5% agarose with 2 mM MgCl$_2$, melted at 65° C. and ligated into a BamHI/Asp718 digested baculovirus expression vector, pFastBac1 (Bac-to-Bac™ System, GIBCO-BRL, Gaithersburg, Md.). Fifty nanograms of the restriction digested zlipo1 insert and 148 ng of the corresponding vector were ligated overnight. The ligation mix was diluted 3 fold in TE (10 mM Tris-HCl, pH 7.5 and 1 mM EDTA).

pFLPE1

A zlipo1 fragment having a C-terminal Glu-Glu tag was generated by PCR as described above using oligonucleotide primers ZC13405 (SEQ ID NO:26) and ZC13403 (SEQ ID NO:28). A fragment of the expected size, 556 bp, was detected by gel electrophoresis and captured as above in pCR2.1 as a plasmid called pLPE1. The DNA fragment was digested from pLPE1 with the restriction enzymes Bgl II and Ap718 and the resulting 539 bp zlipo1 restriction fragment was ligated into a Bam HI/Asp718 digested pFastBac1 vector and transformed into DH10a cells as described above, using 137 ng vector and 48 ng zlipo1 fragment.

Four fmol of the diluted ligation mixes were independently transformed into DH5a Library Efficiency competent cells (Life Technologies), according to manufacturer's direction, by heat shock for 45 seconds in a 42° C. water-bath. The ligated DNA was diluted in the appropriate volume of SOC media (2% Bacto Tryptone, 0.5% Bacto Yeast Extract, 10 ml 1M NaCl, 1.5 mM KCl, 10 mM MgCl$_2$, 10 mM MgSO$_4$ and 20 mM glucose) and plated onto LB plates containing 100 mg/l ampicillin. The plates were incubated overnight at 37° C. Plasmid DNA was prepared using the QiaVac Miniprep8 system (Qiagen) according the manufacturer's directions. The clones were screened by restriction digest with Hind III/BspE1.

One positive construct was chosen for untagged zlipo1 and CEE-tagged zlipo1. One microliter of the plasmid DNA from each of these constructs was used to independently transform 20 microliters DH10Bac Max Efficiency competent cells (GIBCO-BRL, Gaithersburg, Md.) according to manufacturer's instruction, by heat shock at 42° C. for 45 seconds. The transformants were then diluted in an appropriate volume of SOC media SOC media and plated on to Luria Agar plates containing 50 mg/l kanamycin, 7 mg/l gentamicin, 10 mg/l tetracycline, IPTG and Bluo-Gal™ (GibcoBRL). The cells were incubated for 48 hours at 37° C. A color selection was used to identify those cells having virus that had incorporated into the plasmid (referred to as a "bacmid"). Those colonies, which were white in color, were picked for analysis. Bacmid DNA was isolated from positive colonies and screened for the correct insert using PCR. Oligonucleotide primers ZC976 (SEQ ID NO:31) and ZC447 (SEQ ID NO:32) were used and those having the correct insert were used to transfect *Spodoptera frugiperda* (Sf9) cells.

Sf9 cells were seeded at 5×10$^6$ cells per plate and allowed to attach for 1 hour at 27° C. Five microliters of bacmid DNA was diluted with 100 ml Sf-900 II SFM. Six ml of CellFECTIN Reagent (Life Technologies) was diluted with 100 ml Sf-900 II SMF. The bacmid DNA and lipid solutions were gently mixed and incubated 30–45 minutes at room temperature. The media from one plate of cells were aspirated, and the lipid-DNA mixture to which 0.8 ml of Sf-900 II SFM was added. The cells were incubated at 27° C. for 4–5 hours, then 2 ml of Sf-900 II media containing penicillin/streptomycin was added to each plate. The plates were incubated at 27° C., 90% humidity, for 72 hours after which the virus was harvested.

Sf9 cells were grown in 50 ml Sf-900 II SFM in a 50 ml shake flask to an approximate density of $0.04$–$0.50 \times 10^6$ cells/ml. They were then transfected with 50 ml of the virus stock from above and incubated at 27° C. for 4 days after which time the virus was harvested, and titered, $1.08 \times 10^8$ pfu/ml. To scale up, five liters of SF 900 II SFM containing SF 9 cells was incubated at 27° C. and grown for 91 hours. The cells were then transfected with the harvested virus (MOI 0.2) and incubated as above for 71 hours.

EXAMPLE 6
Flag-Tagged zlipo1 from BHK Cells

Unless otherwise noted, all operations were carried out at 4° C. The following procedure was used to purify zlipo1 protein containing N-terminal or C-terminal flag tags. A total of 25 liters of pooled N- and C-terminally FLAG tagged conditioned media from BHK cells was sequentially sterile filtered through a 4 inch, 0.2 mM Millipore OptiCap capsule filter (Millipore, Bedford, Mass.) and a 0.2 mM Gelman Supercap 50 (Gelman, Ann Arbor, Mich.). The material was then concentrated to about 1.3 liters using a Millipore ProFlux A30 tangential flow concentrator (Millipore) fitted with a 3000 kDa cutoff AmiconS10Y3 membrane (Amicon, Bedford, Mass.). The concentrated material was again sterile-filtered with the Gelman filter as described above. A 25.0 ml sample of anti-Flag Sepharose (Eastman Kodak, Rochester, N.Y.) was added to the sample for batch adsorption and the mixture was gently agitated on a roller culture apparatus (Wheaton Millville, N.J.) for 18.0 h at 4° C.

The mixture was then poured into a 5.0×20.0 cm Econo-Column (Bio-Rad, Laboratories, Hercules, Calif.), and the gel was washed with 30 column volumes of phosphate buffered saline (PBS). The unretained flow-through fraction was discarded. Once the absorbance of the effluent at 280 nM was less than 0.05, flow through the column was reduced to zero and the anti-Flag Sepharose gel was washed with 2.0 column volumes of PBS containing 0.2 mg/ml of Flag peptide, N-AspTyrLysAspAspAspAspLys-C (SEQ ID NO: 6). After 1.0 h at 4° C., flow was resumed and the eluted protein was collected. This fraction was referred to as the peptide elution. The anti-Flag Sepharose gel was washed with 2.0 column volumes of 0.1M glycine, pH 2.5, and the glycine wash was collected separately. The pH of the glycine-eluted fraction was adjusted to 7.0 by the addition of a small volume of 10× PBS and stored at 4° C. for future analysis.

The peptide elution was concentrated to 5.0 ml using a 5,000 molecular weight cutoff membrane concentrator (Millipore, Bedford, Mass.) according to the manufacturer's instructions. The concentrated peptide elution was then separated from free peptide by chromatography on a 1.5×50 cm Sephadex G-50 column (Pharmacia, Piscataway, N.J.) equilibrated in PBS at a flow rate of 1.0 ml/min using a BioCad Sprint HPLC system (PerSeptive BioSystems, Framingham, Mass.). Two-ml fractions were collected and the absorbance at 280 nM was monitored. The first peak of material absorbing at 280 nM and eluting near the void volume of the column was collected.

By SDS-PAGE and Western analysis with anti-Flag M2 antibodies (Kodak), the purified, pooled N- and C-terminally FLAG tag zlipo1 protein was composed of approximately equimolar amounts of two Coomassie Blue-stained bands of apparent molecular weights 19,000 and 23,000 that also showed crossreactivity with the anti-Flag M2 antibody. The mobility of each band was the same on SDS-PAGE gels in the presence or absence of reducing agents.

The protein concentration of the purified proteins (0.5 mg/ml) was performed by BCA analysis (Pierce, Rockford, Ill.) and the material was aliquoted, and stored at −80° C.

zlipo1 CEE from Baculovirus Infected Sf9 Cells

Unless otherwise noted, all operations were carried out at 4° C. A mixture of protease inhibitors was added to a 2000 ml sample of conditioned media from baculovirus-infected Sf9 cells to final concentrations of 2.5 mM ethylenediaminetetraacetic acid (EDTA, Sigma Chemical Co. St. Louis, Mo.), 0.001 mM leupeptin (Boehringer-Mannheim, Indianapolis, Ind.), 0.001 mM pepstatin (Boehringer-Mannheim) and 0.4 mM Pefabloc (Boehringer-Mannheim). The sample was centrifuged at 10,000 rpm for 30 min at 4° C. in a Beckman JLA-10.5 rotor (Beckman Instruments, Palo Alto, Calif.) in a Beckman Avanti J25I centrifuge (Beckman Instruments) to remove cell debris. To the supernatant fraction was added a 50.0 ml sample of anti-EE Sepharose, prepared as described below, and the mixture was gently agitated on a Wheaton (Millville, N.J.) roller culture apparatus for 18.0 h at 4° C.

The mixture was then poured into a 5.0×20.0 cm Econo-Column (Bio-Rad, Laboratories, Hercules, Calif.) and the gel was washed with 30 column volumes of phosphate buffered saline (PBS). The unretained flow-through fraction was discarded. Once the absorbance of the effluent at 280 nM was less than 0.05, flow through the column was reduced to zero and the anti-EE Sepharose gel was washed batchwise with 2.0 column volumes of PBS containing 0.4 mg/ml of EE peptide (AnaSpec, San Jose, Calif.). The peptide used has the sequence GluTyrMetProValAsp (SEQ ID NO: 25). After 1.0 h at 4° C., flow was resumed and the eluted protein was collected. This fraction was referred to as the peptide elution. The anti-EE Sepharose gel was then washed with 2.0 column volumes of 0.1M glycine, pH 2.5, and the glycine wash was collected separately. The pH of the glycine-eluted fraction was adjusted to 7.0 by the addition of a small volume of 10× PBS and stored at 4° C. for future analysis if needed.

The peptide elution was concentrated to 5.0 ml using a 5,000 molecular weight cutoff membrane concentrator (Millipore, Bedford, Mass.) according to the manufacturer's instructions. The concentrated peptide elution was then separated from free peptide by chromatography on a 1.5×50 cm Sephadex G-50 (Pharmacia, Piscataway, N.J.) column equilibrated in PBS at a flow rate of 1.0 ml/min using a BioCad Sprint HPLC system (PerSeptive BioSystems, Framingham, Mass.). Two-ml fractions were collected and the absorbance at 280 nM was monitored. The first peak of material absorbing at 280 nM and eluting near the void volume of the column was collected. This represented purified zlipo1 CEE.

By SDS-PAGE and Western analysis, the material was composed of a single band of apparent molecular weight 21,000 that also showed cross-reactivity on Western blots using the anti EE-antibodies. The mobility of the band was the same in the presence and absence of reducing agents. The protein concentration of the purified proteins (0.52 mg/ml) was performed by BCA analysis (Pierce, Rockford, Ill.) and the material was aliquoted, and stored at −80° C. according to our standard procedures.

Preparation of Anti-EE Sepharose

A 100 ml bed volume of protein G-Sepharose (Pharmacia, Piscataway, N.J.) was washed 3 times with 100 ml of PBS containing 0.02% sodium azide using a 500 ml Nalgene 0.45 micron filter unit. The gel was washed with 6.0 volumes of 200 mM triethanolamine, pH 8.2 (TEA, Sigma, St. Louis, Mo.), and an equal volume of EE antibody solution containing 900 mg of antibody was added. After an overnight incubation at 4° C., unbound antibody was removed by washing the resin with 5 volumes of 200 mM TEA as described above. The resin was resuspended in 2 volumes of TEA, transferred to a suitable container, and dimethylpimilimidate-2HCl (Pierce, Rockford, Ill.), dissolved in TEA, was added to a final concentration of 36 mg/ml of gel. The gel was rocked at room temperature for 45 min and the liquid was removed using the filter unit as described above. Nonspecific sites on the gel were then blocked by incubating for 10 min at room temperature with 5 volumes of 20 mM ethanolamine in 200 mM TEA. The gel was then washed with 5 volumes of PBS containing 0.02% sodium azide and stored in this solution at 4° C.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. An isolated polypeptide comprising a sequence of amino acid residues as shown in SEQ ID NO: 2 from amino acid residue 1 or 17 to residue 170.

2. A pharmaceutical composition comprising a polypeptide comprising a sequence of amino acid residues as shown in SEQ ID NO: 2 from residue 1 or 17 to residue 170, in combination with a pharmaceutically acceptable vehicle.

3. A fusion protein comprising a first polypeptide comprising a sequence of amino acid residues as shown in SEQ ID NO: 2 from residue 1 or 17 to residue 170 and a second moiety.

4. The fusion protein of claim 3, wherein the protein further comprises one or more cleavage sites.

5. The fusion protein of claim 3, wherein the second moiety is selected from the group consisting of:

a secretory signal sequence;

von Ebner's gland protein;

epididymal-retinoic acid binding protein; and an affinity tag.

* * * * *

SEQUENCE LISTING

<160> NUMBER OF SEQ ID NOS: 30

<210> SEQ ID NO 1
<211> LENGTH: 522
<212> TYPE: DNA
<213> ORGANISM: Homo sapiens
<220> FEATURE:
<221> NAME/KEY: CDS
<222> LOCATION: (7)...(516)

<400> SEQUENCE: 1

```
ctcgag atg aag acc ctg ttc ctg ggt gtc acg ctc ggc ctg gcc gct        48
       Met Lys Thr Leu Phe Leu Gly Val Thr Leu Gly Leu Ala Ala
         1               5                  10 gcc ctg tcc ttc acc ctg gag gag gag gat atc aca ggg acc tgg tac        96
Ala Leu Ser Phe Thr Leu Glu Glu Glu Asp Ile Thr Gly Thr Trp Tyr
 15                  20                  25                  30 gtg aag gcc atg gtg gtc gat aag gac ttt ccg gag gac agg agg ccc       144
Val Lys Ala Met Val Val Asp Lys Asp Phe Pro Glu Asp Arg Arg Pro
                     35                  40                  45 agg aag gtg tcc cca gtg aag gtg aca gcc ctg ggc ggt ggg aag ttg       192
Arg Lys Val Ser Pro Val Lys Val Thr Ala Leu Gly Gly Gly Lys Leu
                 50                  55                  60 gaa gcc acg ttc acc ttc atg agg gag gat cgg tgc atc cag aag aaa       240
Glu Ala Thr Phe Thr Phe Met Arg Glu Asp Arg Cys Ile Gln Lys Lys
 65                  70                  75 atc ctg atg cgg aag acg gag gag cct ggc aaa tac agc gcc tat ggg       288
Ile Leu Met Arg Lys Thr Glu Glu Pro Gly Lys Tyr Ser Ala Tyr Gly
 80                  85                  90 ggc agg aag ctc atg tac ctg cag gag ctg ccc agg agg gac cac tac       336
Gly Arg Lys Leu Met Tyr Leu Gln Glu Leu Pro Arg Arg Asp His Tyr
 95                 100                 105                 110 atc ttt tac tgc aaa gac cag cac cat ggg ggc ctg ctc cac atg gga       384
Ile Phe Tyr Cys Lys Asp Gln His His Gly Gly Leu Leu His Met Gly
                    115                 120                 125 aag ctt gtg ggt agg aat tct gat acc aac cgg gag gcc ctg gaa gaa       432
Lys Leu Val Gly Arg Asn Ser Asp Thr Asn Arg Glu Ala Leu Glu Glu
                130                 135                 140 ttt aag aaa ttg gtg cag cgc aag gga ctc tcg gag gag gac att ttc       480
Phe Lys Lys Leu Val Gln Arg Lys Gly Leu Ser Glu Glu Asp Ile Phe
```

```
                145                 150                 155
acg ccc ctg cag acg gga agc tgc gtt ccc gaa cac ggatcc                    522
Thr Pro Leu Gln Thr Gly Ser Cys Val Pro Glu His
    160                 165                 170
```

<210> SEQ ID NO 2
<211> LENGTH: 170
<212> TYPE: PRT
<213> ORGANISM: Homo sapiens

<400> SEQUENCE: 2

```
Met Lys Thr Leu Phe Leu Gly Val Thr Leu Gly Leu Ala Ala Ala Leu
 1               5                  10                  15

Ser Phe Thr Leu Glu Glu Glu Asp Ile Thr Gly Thr Trp Tyr Val Lys
                20                  25                  30

Ala Met Val Val Asp Lys Asp Phe Pro Glu Asp Arg Arg Pro Arg Lys
             35                  40                  45

Val Ser Pro Val Lys Val Thr Ala Leu Gly Gly Lys Leu Glu Ala
         50                  55                  60

Thr Phe Thr Phe Met Arg Glu Asp Arg Cys Ile Gln Lys Lys Ile Leu
65                  70                  75                  80

Met Arg Lys Thr Glu Glu Pro Gly Lys Tyr Ser Ala Tyr Gly Gly Arg
                85                  90                  95

Lys Leu Met Tyr Leu Gln Glu Leu Pro Arg Arg Asp His Tyr Ile Phe
            100                 105                 110

Tyr Cys Lys Asp Gln His His Gly Gly Leu Leu His Met Gly Lys Leu
        115                 120                 125

Val Gly Arg Asn Ser Asp Thr Asn Arg Glu Ala Leu Glu Glu Phe Lys
    130                 135                 140

Lys Leu Val Gln Arg Lys Gly Leu Ser Glu Glu Asp Ile Phe Thr Pro
145                 150                 155                 160

Leu Gln Thr Gly Ser Cys Val Pro Glu His
                165                 170
```

<210> SEQ ID NO 3
<211> LENGTH: 22
<212> TYPE: DNA
<213> ORGANISM: Artificial Sequence
<220> FEATURE:
<223> OTHER INFORMATION: oligonucleotide primer: ZC13139

<400> SEQUENCE: 3
aatggttcgt cctgggcctg gc                                              22

<210> SEQ ID NO 4
<211> LENGTH: 24
<212> TYPE: DNA
<213> ORGANISM: Artificial Sequence
<220> FEATURE:
<223> OTHER INFORMATION: oligonucleotide primer: ZC13937

<400> SEQUENCE: 4
acacctcaaa gcggccatca tcac                                            24

<210> SEQ ID NO 5
<211> LENGTH: 510
<212> TYPE: DNA
<213> ORGANISM: Artificial Sequence
<220> FEATURE:
<223> OTHER INFORMATION: Degenerate sequence derived from human zlipo1
      nucleotide sequence <220> FEATURE:
<221> NAME/KEY: variation
<222> LOCATION: (1)...(510)
<223> OTHER INFORMATION: n is any nucleotide

<400> SEQUENCE: 5

| | | | | | |
|---|---|---|---|---|---|
| atgaaracny | tnttyytngg | ngtnacnytn | ggnytngcng | cngcnytnws | nttyacnytn | 60 |
| gargargarg | ayathacngg | nacntggtay | gtnaargcna | tggtngtnga | yaargaytty | 120 |
| ccngargaym | gnmgnccnmg | naargtnwsn | ccngtnaarg | tnacngcnyt | nggnggnggn | 180 |
| aarytngarg | cnacnttyac | nttyatgmgn | gargaymgnt | gyathcaraa | raarathytn | 240 |
| atgmgnaara | cngargarcc | nggnaartay | wsngcntayg | gnggnmgnaa | rytnatgtay | 300 |
| ytncargary | tnccnmgnmg | ngaycaytay | athttytayt | gyaargayca | rcaycayggn | 360 |
| ggnytnytnc | ayatgggnaa | rytngtnggn | mgnaaywsng | ayacnaaymg | ngargcnytn | 420 |
| gargarttya | araarytngt | ncarmgnaar | ggnytnwsng | argargayat | httyacnccn | 480 |
| ytncaracng | gnwsntgygt | nccngarcay | | | | 510 |

<210> SEQ ID NO 6
<211> LENGTH: 8
<212> TYPE: PRT
<213> ORGANISM: Artificial Sequence
<220> FEATURE:
<223> OTHER INFORMATION: Flag affinity peptide

<400> SEQUENCE: 6

Asp Tyr Lys Asp Asp Asp Asp Lys
 1               5

<210> SEQ ID NO 7
<211> LENGTH: 5
<212> TYPE: PRT
<213> ORGANISM: Artificial Sequence
<220> FEATURE:
<223> OTHER INFORMATION: Glu-Glu affinity peptide

<400> SEQUENCE: 7

Glu Tyr Pro Met Glu
 1               5

<210> SEQ ID NO 8
<211> LENGTH: 30
<212> TYPE: DNA
<213> ORGANISM: Artificial Sequence
<220> FEATURE:
<223> OTHER INFORMATION: Oligonucleotide primer: ZC13290

<400> SEQUENCE: 8
ggatctagac tagtgttcgg gaacgcagct                                    30

<210> SEQ ID NO 9
<211> LENGTH: 30
<212> TYPE: DNA
<213> ORGANISM: Artificial Sequence
<220> FEATURE:
<223> OTHER INFORMATION: Oligonucleotide primer: ZC13291

<400> SEQUENCE: 9
cctggatccc tgtccttcac cctggaggag                                    30

<210> SEQ ID NO 10
<211> LENGTH: 30
<212> TYPE: DNA

<213> ORGANISM: Artificial Sequence
<220> FEATURE:
<223> OTHER INFORMATION: Oligonucleotide primer: ZC13270

<400> SEQUENCE: 10
ggactcgaga tgaagaccct gttcctgggt                                        30

<210> SEQ ID NO 11
<211> LENGTH: 30
<212> TYPE: DNA
<213> ORGANISM: Artificial Sequence
<220> FEATURE:
<223> OTHER INFORMATION: Oligonucleotide primer: ZC13271

<400> SEQUENCE: 11
cctggatccg tgttcgggaa cgcagcttcc                                        30

<210> SEQ ID NO 12
<211> LENGTH: 51
<212> TYPE: DNA
<213> ORGANISM: Artificial Sequence
<220> FEATURE:
<223> OTHER INFORMATION: Oligonucleotide primer: ZC13731

<400> SEQUENCE: 12
ggtgtaagct tggacaagag agaagaagaa tacatgccaa tggaaggtgg t                51

<210> SEQ ID NO 13
<211> LENGTH: 63
<212> TYPE: DNA
<213> ORGANISM: Artificial Sequence
<220> FEATURE:
<223> OTHER INFORMATION: Oligonucleotide primer: ZC13762

<400> SEQUENCE: 13
ggtccctgtg atatcctcct cctccagggt gaaggacaga ccaccttcca ttggcatgta       60
ttc                                                                    63

<210> SEQ ID NO 14
<211> LENGTH: 44
<212> TYPE: DNA
<213> ORGANISM: Artificial Sequence
<220> FEATURE:
<223> OTHER INFORMATION: Oligonucleotide primer: ZC13497

<400> SEQUENCE: 14
agcattgctg ctaaagaaga aggtgtaagc ttggacaaga gaga                        44

<210> SEQ ID NO 15
<211> LENGTH: 52
<212> TYPE: DNA
<213> ORGANISM: Artificial Sequence
<220> FEATURE:
<223> OTHER INFORMATION: Oligonucleotide primer: ZC13764

<400> SEQUENCE: 15
cttatcgacc accatggcct tcacgtacca ggtccctgtg atatcctcct cc               52

<210> SEQ ID NO 16
<211> LENGTH: 147
<212> TYPE: DNA
<213> ORGANISM: Artificial Sequence
<220> FEATURE:
<223> OTHER INFORMATION: NEE-tagged linker

<400> SEQUENCE: 16
agcattgctg ctaaagaaga aggtgtaagc ttggacaaga gagaagaaga atacatgcca    60
atggaaggtg gtctgtcctt caccctggag gaggaggata tcacagggac ctggtacgtg   120
aaggccatgg tggtcgataa ggacttt                                      147

<210> SEQ ID NO 17
<211> LENGTH: 147
<212> TYPE: DNA
<213> ORGANISM: Artificial Sequence
<220> FEATURE:
<223> OTHER INFORMATION: C-terminal 3' linker

<400> SEQUENCE: 17
cgcaagggac tctcggagga ggacattttc actcccctgc agacgggaag ctgcgttccc    60
gaacactgat agtattctag ggctgcctgt ttggatattt ttataatttt tgagagtttg   120
ccaactaatg ttttctctt ctatgat                                       147

<210> SEQ ID NO 18
<211> LENGTH: 52
<212> TYPE: DNA
<213> ORGANISM: Artificial Sequence
<220> FEATURE:
<223> OTHER INFORMATION: Oligonucleotide primer: ZC13734

<400> SEQUENCE: 18
atcatagaag agaaaaacat tagttggcaa actctcaaaa attataaaaa ta            52

<210> SEQ ID NO 19
<211> LENGTH: 51
<212> TYPE: DNA
<213> ORGANISM: Artificial Sequence
<220> FEATURE:
<223> OTHER INFORMATION: Oligonucleotide primer: ZC13727

<400> SEQUENCE: 19
cgcaagggac tctcggagga ggacattttc actcccctgc agacgggaag c             51

<210> SEQ ID NO 20
<211> LENGTH: 63
<212> TYPE: DNA
<213> ORGANISM: Artificial Sequence
<220> FEATURE:
<223> OTHER INFORMATION: Oligonucleotide primer: ZC13725

<400> SEQUENCE: 20
actcccctgc agacgggaag ctgcgttccc gaacactgat agtattctag ggctgcctgt    60
ttg                                                                 63

<210> SEQ ID NO 21
<211> LENGTH: 54
<212> TYPE: DNA
<213> ORGANISM: Artificial Sequence
<220> FEATURE:
<223> OTHER INFORMATION: Oligonucleotide primer: ZC13733

<400> SEQUENCE: 21
tggcaaactc tcaaaaatta taaaatatc caaacaggca gccctagaat acta           54

<210> SEQ ID NO 22
<211> LENGTH: 51
<212> TYPE: DNA
<213> ORGANISM: Artificial Sequence
<220> FEATURE:

```
<223> OTHER INFORMATION: Oligonucleotide primer: ZC13735

<400> SEQUENCE: 22
ggtgtaagct tggacaagag agattacaag gacgatgatg acaagggtgg t          51

<210> SEQ ID NO 23
<211> LENGTH: 61
<212> TYPE: DNA
<213> ORGANISM: Artificial Sequence
<220> FEATURE:
<223> OTHER INFORMATION: Oligonucleotide primer: ZC13839

<400> SEQUENCE: 23
ggtccctgtg atatcctcct cctccagggt gaaggacaga ccaccttgt catcatcgtc    60 c                                                                  61

<210> SEQ ID NO 24
<211> LENGTH: 147
<212> TYPE: DNA
<213> ORGANISM: Artificial Sequence
<220> FEATURE:
<223> OTHER INFORMATION: N-terminal Flag linker

<400> SEQUENCE: 24
agcattgctg ctaaagaaga aggtgtaagc ttggacaaga gagattacaa ggacgatgat    60
gacaagggtg gtctgtcctt caccctggag gaggaggata tcacagggac ctggtacgtg   120
aaggccatgg tggtcgataa ggacttt                                       147

<210> SEQ ID NO 25
<211> LENGTH: 6
<212> TYPE: PRT
<213> ORGANISM: Artificial Sequence
<220> FEATURE:
<223> OTHER INFORMATION: Glu-Glu elution peptide

<400> SEQUENCE: 25

Glu Tyr Met Pro Val Asp
 1               5

<210> SEQ ID NO 26
<211> LENGTH: 38
<212> TYPE: DNA
<213> ORGANISM: Artificial Sequence
<220> FEATURE:
<223> OTHER INFORMATION: Oligonucleotide primer: ZC13405

<400> SEQUENCE: 26
cagagagatc tccatgaaga ccctgttcct gggtgtca                           38

<210> SEQ ID NO 27
<211> LENGTH: 31
<212> TYPE: DNA
<213> ORGANISM: Artificial Sequence
<220> FEATURE:
<223> OTHER INFORMATION: Oligonucleotide primer: ZC13406

<400> SEQUENCE: 27 gggggggtacc tagtgttcgg gaacgcagct t                                 31

<210> SEQ ID NO 28
<211> LENGTH: 52
<212> TYPE: DNA
<213> ORGANISM: Artificial Sequence
<220> FEATURE:
```

-continued

<223> OTHER INFORMATION: Oligonucleotide primer: ZC13403

<400> SEQUENCE: 28 gggggtacc tattccatcg gcatgtattc ttcgtgttcg ggaacgcagc tt          52

<210> SEQ ID NO 29
<211> LENGTH: 176
<212> TYPE: PRT
<213> ORGANISM: Homo sapiens

<400> SEQUENCE: 29

```
Met Lys Pro Leu Leu Leu Ala Val Ser Leu Gly Leu Ile Ala Ala Leu
 1               5                  10                  15

Gln Ala His His Leu Leu Ala Ser Asp Glu Glu Ile Gln Asp Val Ser
             20                  25                  30

Gly Thr Trp Tyr Leu Lys Ala Met Thr Val Asp Arg Glu Phe Pro Glu
         35                  40                  45

Met Asn Leu Glu Ser Val Thr Pro Met Thr Leu Thr Thr Leu Glu Gly
     50                  55                  60

Gly Asn Leu Glu Ala Lys Val Thr Met Leu Ile Ser Gly Arg Cys Gln
 65                  70                  75                  80

Glu Val Lys Ala Val Leu Glu Lys Thr Asp Glu Pro Gly Lys Tyr Thr
                 85                  90                  95

Ala Asp Gly Gly Lys His Val Ala Tyr Ile Ile Arg Ser His Val Lys
            100                 105                 110

Asp His Tyr Ile Phe Tyr Cys Glu Gly Glu Leu His Gly Lys Pro Val
        115                 120                 125

Arg Gly Val Lys Leu Val Gly Arg Asp Pro Lys Asn Asn Leu Glu Ala
    130                 135                 140

Leu Glu Asp Phe Glu Lys Ala Ala Gly Ala Arg Gly Leu Ser Thr Glu
145                 150                 155                 160

Ser Ile Leu Ile Pro Arg Gln Ser Glu Thr Cys Ser Pro Gly Ser Asp
                165                 170                 175
```

<210> SEQ ID NO 30
<211> LENGTH: 188
<212> TYPE: PRT
<213> ORGANISM: Rattus norvegicus

<400> SEQUENCE: 30

```
Met Glu Asn Ile Met Pro Phe Ala Leu Leu Gly Leu Cys Val Gly Leu
 1               5                  10                  15

Ala Ala Gly Thr Glu Gly Ala Val Val Lys Asp Phe Asp Ile Ser Lys
             20                  25                  30

Phe Leu Gly Phe Trp Tyr Glu Ile Ala Phe Ala Ser Lys Met Gly Thr
         35                  40                  45

Pro Gly Leu Ala His Lys Glu Glu Lys Met Gly Ala Met Val Val Glu
     50                  55                  60

Leu Lys Glu Asn Leu Leu Ala Leu Thr Thr Thr Tyr Tyr Ser Glu Asp
 65                  70                  75                  80

His Cys Val Leu Glu Lys Val Thr Ala Thr Glu Gly Asp Gly Pro Ala
                 85                  90                  95

Lys Phe Gln Val Thr Arg Leu Ser Gly Lys Lys Glu Val Val Val Glu
            100                 105                 110

Ala Thr Asp Tyr Leu Thr Tyr Ala Ile Ile Asp Ile Thr Ser Leu Val
        115                 120                 125
```

```
Ala Gly Ala Val His Arg Thr Met Lys Leu Tyr Ser Arg Ser Leu Asp
    130             135             140

Asp Asn Gly Glu Ala Leu Tyr Asn Phe Arg Lys Ile Thr Ser Asp His
145             150             155             160

Gly Phe Ser Glu Thr Asp Leu Tyr Ile Leu Lys His Asp Leu Thr Cys
            165             170             175

Val Lys Val Leu Gln Ser Ala Ala Glu Ser Arg Pro
        180             185
```